US012653231B2

(12) United States Patent
Lei et al.

(10) Patent No.: US 12,653,231 B2
(45) Date of Patent: Jun. 16, 2026

(54) ELECTRONIC ATOMIZATION DEVICE AND AIR CURTAIN FORMATION STRUCTURE USED BY SAME

(71) Applicant: SHENZHEN SMOORE TECHNOLOGY LIMITED, Shenzhen (CN)

(72) Inventors: Guilin Lei, Shenzhen (CN); Dan Xu, Shenzhen (CN); Guangwu Tang, Shenzhen (CN); Ru Jiang, Shenzhen (CN); Boxue Gong, Shenzhen (CN); Shiyi Cheng, Shenzhen (CN); Pan Xie, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 675 days.

(21) Appl. No.: 17/820,801

(22) Filed: Aug. 18, 2022

(65) Prior Publication Data

US 2022/0386691 A1 Dec. 8, 2022

Related U.S. Application Data

(63) Continuation of application No. PCT/CN2020/110870, filed on Aug. 24, 2020.

(30) Foreign Application Priority Data

Feb. 20, 2020 (CN) .......................... 202010105137.9

(51) Int. Cl.
*A24F 40/40* (2020.01)
*A24F 7/00* (2006.01)
(Continued)

(52) U.S. Cl.
CPC ................ *A24F 40/40* (2020.01); *A24F 7/00* (2013.01); *A24F 40/10* (2020.01); *A24F 40/48* (2020.01);
(Continued)

(58) Field of Classification Search
None
See application file for complete search history.

(56) References Cited

U.S. PATENT DOCUMENTS 5,012,804 A 5/1991 Foley et al.
5,040,527 A 8/1991 Larson et al.
(Continued)

FOREIGN PATENT DOCUMENTS

CN 1285759 A 2/2001
CN 1387447 A 12/2002
(Continued)

OTHER PUBLICATIONS

CN 204907913, EPO machine translation of document submitted by Applicant via IDS Sep. 26, 2023 (Year: 2015).*
(Continued)

*Primary Examiner* — Michael H. Wilson
*Assistant Examiner* — Michael T Fulton
(74) *Attorney, Agent, or Firm* — Leydig, Voit & Mayer, Ltd.

(57) ABSTRACT

An air-curtain forming structure applicable to an electronic vaporization device includes: an airflow channel for delivering vapor; and a first air inlet channel in communication with the airflow channel and for introducing an external airflow into the airflow channel so as to form a blocking airflow between an inner wall of the airflow channel and the vapor.

36 Claims, 21 Drawing Sheets

(51) Int. Cl.

| | | |
|---|---|---|
| *A24F 40/10* | (2020.01) | |
| *A24F 40/48* | (2020.01) | |
| *A61M 11/04* | (2006.01) | |
| *A61M 15/00* | (2006.01) | |
| *A61M 15/06* | (2006.01) | |

(52) U.S. Cl.

CPC ...... *A61M 11/042* (2014.02); *A61M 15/0021* (2014.02); *A61M 15/06* (2013.01)

(56) References Cited

U.S. PATENT DOCUMENTS

| | | | |
|---|---|---|---|
| 5,435,297 A | 7/1995 | Klein | |
| 10,098,381 B2 | 10/2018 | Kane et al. | |
| 10,292,424 B2 * | 5/2019 | Brammer | A24F 40/48 |
| 2011/0011395 A1 | 1/2011 | Mazela et al. | |
| 2013/0000641 A1 | 1/2013 | Mazela et al. | |
| 2014/0158123 A1 | 6/2014 | Mazela et al. | |
| 2014/0261492 A1 | 9/2014 | Kane et al. | |
| 2016/0198772 A1 | 7/2016 | Thorens et al. | |
| 2019/0150519 A1 | 5/2019 | Liu et al. | |
| 2019/0373949 A1 | 12/2019 | Pan | |
| 2019/0380387 A1 * | 12/2019 | Rose | A24F 7/00 |

FOREIGN PATENT DOCUMENTS

| | | | | | |
|---|---|---|---|---|---|
| CN | 1541125 | A | | 10/2004 | |
| CN | 101980738 | A | | 2/2011 | |
| CN | 103041480 | A | | 4/2013 | |
| CN | 104736191 | A | | 6/2015 | |
| CN | 204907913 | U | * | 12/2015 | A24F 47/008 |
| CN | 205456063 | U | | 8/2016 | |
| CN | 205547375 | U | | 9/2016 | |
| CN | 105982363 | A | | 10/2016 | |
| CN | 205848684 | U | | 1/2017 | |
| CN | 206525551 | U | | 9/2017 | |
| CN | 107440161 | A | | 12/2017 | |
| CN | 107581662 | A | | 1/2018 | |
| CN | 208355880 | U | | 1/2019 | |
| CN | 109718431 | A | | 5/2019 | |
| CN | 110250579 | A | | 9/2019 | |
| CN | 110558630 | A | | 12/2019 | |
| CN | 110613171 | A | | 12/2019 | |
| CN | 110623308 | A | | 12/2019 | |
| CN | 111359060 | A | | 7/2020 | |
| DE | 9204938 | U1 | | 8/1993 | |
| DE | 102018112711 | A1 | | 11/2019 | |
| GB | 2279879 | A | | 1/1995 | |
| WO | 0136033 | A2 | | 5/2001 | |
| WO | WO-2004041338 | A1 | * | 5/2004 | A61M 15/0086 |
| WO | 2014029827 | A1 | | 2/2014 | |
| WO | 2015112750 | A1 | | 7/2015 | |
| WO | 2017167512 | A1 | | 10/2017 | |
| WO | 2018112755 | A1 | | 6/2018 | |
| WO | 2018120206 | A1 | | 7/2018 | |
| WO | 2019145159 | A1 | | 8/2019 | |
| WO | 2019234055 | A1 | | 12/2019 | |

OTHER PUBLICATIONS

Patent Cooperation Treaty, International Search Report, International Application No. PCT/CN2020/110870 (Nov. 23, 2020).
Patent Cooperation Treaty, Written Opinion of the International Searching Authority, International Application No. PCT/CN2020/110870 (Nov. 23, 2020).
Chinese Patent Office, First Office Action in Chinese Patent Application No. 202010955466.2 (Aug. 3, 2022).
Patent Cooperation Treaty, International Search Report, International Application No. PCT/CN2021/072494 (Apr. 22, 2021).
Patent Cooperation Treaty, Written Opinion of the International Searching Authority, International Application No. PCT/CN2021/072494 (Apr. 22, 2021).
Patent Cooperation Treaty, International Search Report, International Application No. PCT/CN2020/110872 (Nov. 23, 2020).
Patent Cooperation Treaty, Written Opinion of the International Searching Authority, International Application No. PCT/CN2020/110872 (Nov. 23, 2020).
Patent Cooperation Treaty, International Search Report, International Application No. PCT/CN2020/114886 (Nov. 30, 2020).
Patent Cooperation Treaty, Written Opinion of the International Searching Authority, International Application No. PCT/CN2020/114886 (Nov. 30, 2020).
Chinese Patent Office, Rejection Decision in Chinese Patent Application No. 202010859845.1 (Sep. 5, 2023).
Chinese Patent Office, Rejection Decision in Chinese Patent Application No. 202010955466.2 (Jul. 21, 2023).
Chinese Patent Office, Office Action in Chinese Patent Application No. 202010859845.1 (Jul. 5, 2023).
Chinese Patent Office, Office Action in Chinese Patent Application No. 202010859124.0 (Aug. 7, 2023).
European Patent Office, Search Report in European Patent Application No. 20920396.7 (Aug. 3, 2023).
Chinese Patent Office, Office Action in Chinese Patent Application No. 202010955466.2 (Feb. 28, 2023).
Chinese Patent Office, Office Action in Chinese Patent Application No. 202010955466.2 (Feb. 23, 2024).
Chinese Patent Office, Notification to Grant Patent Right for Invention in Chinese Patent Application No. 202010859124.0 (Jan. 2, 2024).
Chinese Patent Office, Office Action in Chinese Patent Application No. 202010859845.1 (Jan. 12, 2023).
Chinese Patent Office, Office Action in Chinese Patent Application No. 202010859124.0 (Jan. 20, 2023).
Chinese Patent Office, Third Office Action in Chinese Patent Application No. 202010859845.1 (Apr. 13, 2024).
Chinese Patent Office, Notification to Grant Patent Right for Invention in Chinese Patent Application No. 202010859845.1 (May 29, 2024).
Chinese Patent Office, Fourth Office Action in Chinese Patent Application No. 202010955466.2 (Apr. 11, 2024).
Chinese Patent Office, Notification to Grant Patent Right for Invention in Chinese Patent Application No. 202010955466.2 (May 29, 2024).
U.S. Patent and Trademark Office, Office Action in U.S. Appl. No. 17/820,939 (Mar. 27, 2026).

* cited by examiner 111   214   215   12   213

212

14

211

15

22

15

152

12

22

(a)

(b)

(a)

(b)

(a)                                      (b)

(a)                 (b)

ELECTRONIC ATOMIZATION DEVICE AND AIR CURTAIN FORMATION STRUCTURE USED BY SAME

CROSS-REFERENCE TO PRIOR APPLICATION

This application is a continuation of International Patent Application No. PCT/CN2020/110870, filed on Aug. 24, 2020, which claims priority to Chinese Patent Application No. CN 202010105137.9, filed on Feb. 20, 2020. The entire disclosure of both applications is hereby incorporated by reference herein.

FIELD

This application relates to the technical field of vaporization apparatuses, and in particular, to an electronic vaporization device and an air-curtain forming structure applied thereto.

BACKGROUND

For an existing electronic vaporization device such as an e-cigarette or a medical vaporizer, condensation is prone to occur when vapor comes into contact with an inner wall of the electronic vaporization device. For example, condensate formed on an inner wall of an air outlet channel of the e-cigarette is likely to enter a user's mouth, causing a negative impact on the user experience. For the medical vaporizer, and in particular, for a medical vaporizer configured to deliver drugs to the lungs, vapor carrying the drugs is condensed in the air outlet channel, causing drug loss. In addition, condensate droplets are easily formed not only in the air outlet channel, but also on other inner walls of the electronic vaporization device in contact with the vapor, and consequently, condensate leakage is prone to occur.

SUMMARY

In an embodiment, the present invention provides an air-curtain forming structure applicable to an electronic vaporization device, comprising: an airflow channel configured to deliver vapor; and a first air inlet channel in communication with the airflow channel and configured to introduce an external airflow into the airflow channel so as to form a blocking airflow between an inner wall of the airflow channel and the vapor.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
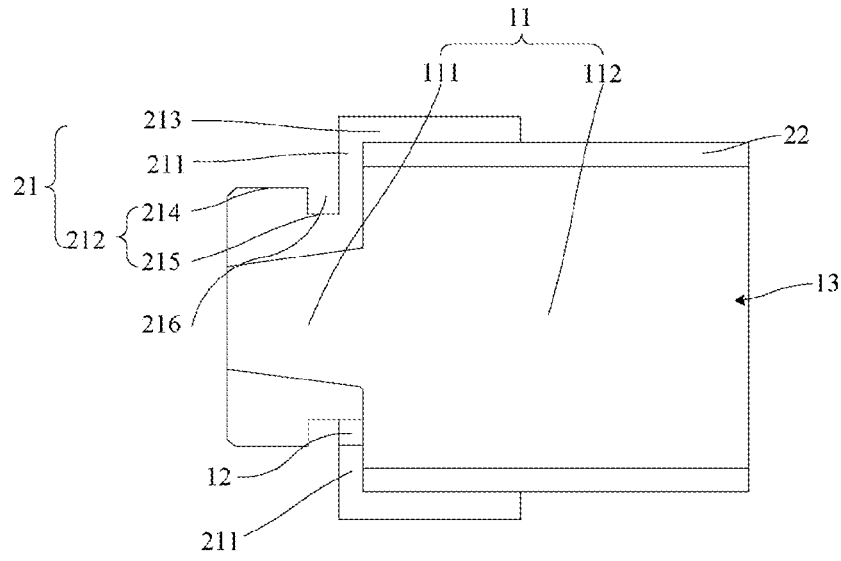
FIG. 1 is a schematic structural diagram of a first embodiment of a vaporization suction nozzle according to this application.

In an embodiment, the present invention provides an electronic vaporization device and an air-curtain forming structure applied thereto, to alleviate the problem of vapor condensation.

In an embodiment, the present invention provides an air-curtain forming structure applicable to an electronic vaporization device. The air-curtain forming structure includes an airflow channel configured to deliver vapor. The air-curtain forming structure further includes a first air inlet channel in communication with the airflow channel, and the first air inlet channel is configured to introduce an external airflow into the airflow channel, so that a blocking airflow is formed between an inner wall of the airflow channel and the vapor.

To resolve the foregoing technical problem, another technical solution adopted in this application is: providing an electronic vaporization device. The electronic vaporization device includes a main body and an air-curtain forming structure, where the main body is connected to the air-curtain forming structure. The air-curtain forming structure further includes a first air inlet channel in communication with the airflow channel, and the first air inlet channel is configured to introduce an external airflow into the airflow channel, so that a blocking airflow is formed between an inner wall of the airflow channel and the vapor.

Beneficial effects of this application are as follows: Compared with the related art, this application provides an electronic vaporization device and an air-curtain forming structure applied thereto. The air-curtain forming structure includes an airflow channel configured to deliver vapor. The airflow channel includes a first air inlet channel, and the first air inlet channel is configured to introduce an external airflow into the airflow channel, so that a blocking airflow is formed between an inner wall of the airflow channel and the vapor. In this application, the blocking airflow is used to block the inner wall of the airflow channel and the vapor, so that the vapor is in contact with the inner wall of the airflow channel as little as possible, the problem of vapor condensation can be alleviated, and less condensate is generated, thereby improving the user experience, reducing drug loss, and reducing the risk of condensate leakage.

In order to make the objects, technical solutions, and advantages of this application clearer, the technical solutions in the embodiments of this application will be clearly and comprehensively described below with reference to the embodiments of this application. Apparently, the described embodiments are some rather than all of the embodiments of this application. All other embodiments obtained by a person of ordinary skill in the art based on the embodiments of this application without creative efforts shall fall within the protection scope of this application. The following embodiments and features in the embodiments may be combined with each other in case that no conflict occurs.

To resolve the technical problem of relatively severe vapor condensation in the related art, an embodiment of this application provides an air-curtain forming structure applicable to an electronic vaporization device. The air-curtain forming structure includes an airflow channel configured to deliver vapor. The air-curtain forming structure further includes a first air inlet channel in communication with the airflow channel, and the first air inlet channel is configured to introduce an external airflow into the airflow channel, so that a blocking airflow is formed between an inner wall of the airflow channel and the vapor. Detailed descriptions are provided below.

Referring to FIG. 1, FIG. 1 is a schematic structural diagram of a first embodiment of a vaporization suction nozzle according to this application.

An exemplary embodiment in which the air-curtain forming structure is a vaporization suction nozzle applicable to the electronic vaporization device is described below.

In this embodiment, the air-curtain forming structure is in a form of the vaporization suction nozzle. The vaporization suction nozzle provided in this embodiment is applicable to electronic vaporization devices such as an e-cigarette and a medical vaporizer. Specifically, the vaporization suction nozzle includes an airflow channel 11. The airflow channel 11 is configured to deliver vapor. The vaporization suction nozzle further includes a first air inlet channel 12 in communication with the airflow channel 11, and the first air inlet channel 12 is configured to introduce an external airflow into the airflow channel 11, so that a blocking airflow is formed between an inner wall of the airflow channel 11 and the vapor. The blocking airflows form an air curtain.

Further, the vaporization suction nozzle further includes an air outlet 13 in communication with the airflow channel 11, the first air inlet channel 12 is close to the inner wall of the airflow channel 11, and an exit of the first air inlet channel 12 faces the air outlet 13, to ensure that the airflow flowing into the airflow channel 11 through the first air inlet channel 12 can flow along the inner wall of the airflow channel 11, that is, the blocking airflow is formed to block the vapor and the inner wall of the airflow channel 11, so that the vapor may be in contact with the inner wall of the airflow channel 11 as little as possible, thereby alleviating the problem of vapor condensation and reducing condensate generation.

Specifically, the vaporization suction nozzle includes an airway body 21 and a suction nozzle portion. The suction nozzle portion includes a tube body 22, and the airflow channel 11 is provided in the airway body 21 and the tube body 22. An end of the tube body 22 away from the airway body 21 is the air outlet 13. The first air inlet channel 12 is provided at a position of the airway body 21 close to an inner wall of the tube body 22, to form a blocking airflow between the inner wall of the tube body 22 and the vapor.

The airflow channel 11 includes an entrance channel 111 and an air guide channel 112. The tube body 22 includes the air guide channel 112. The airway body 21 is mounted at one end of the tube body 22, the airway body 21 includes the entrance channel 111, and the entrance channel 111 of the airway body 21 is in communication with the air guide channel 112 of the tube body 22. The entrance channel 111 is configured to introduce the vapor and deliver the vapor into the air guide channel 112.

Figure 2:
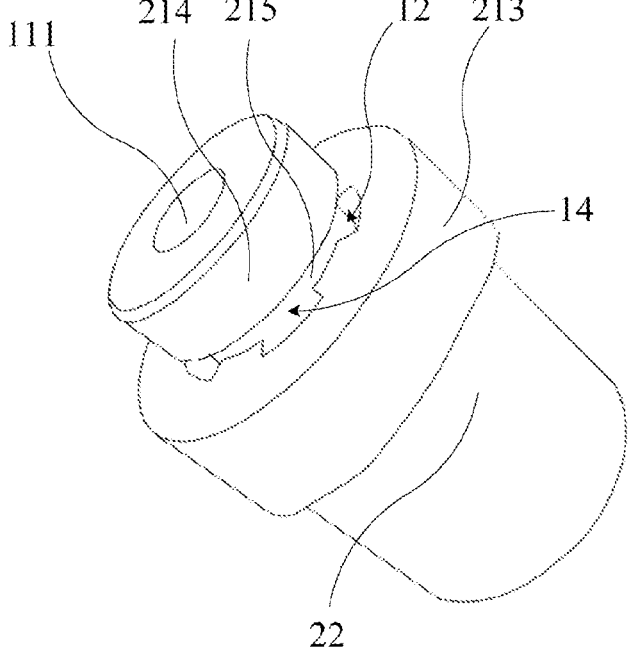
FIG. 2 is a schematic three-dimensional structural diagram of a first embodiment of a vaporization suction nozzle according to this application.

Referring to FIG. 1 and FIG. 2, FIG. 2 is a schematic three-dimensional structural diagram of a first embodiment of a vaporization suction nozzle according to this application. When the airway body 21 is mounted at one end of the tube body 22, a part of the airway body 21 abuts against an end of the air guide channel 112 and covers a part of the air guide channel 112. The first air inlet channel 12 in communication with the air guide channel 112 is provided at a position where the airway body 21 covers the air guide channel 112. Optionally, the airway body 21 includes a wall portion 211 abutting against one end of the air guide channel 112 and covering the part of the air guide channel 112, and the first air inlet channel 12 is located on the wall portion 211 and is in communication with the air guide channel 112.

Condensate is easily formed on an inner wall of the air guide channel 112 due to moisture in the vapor. The first air inlet channel 12 is provided, and air is introduced into the first air inlet channel 12. When inhaling is performed on the vaporization suction nozzle, that is, the vapor is inhaled from the end of the tube body 22 away from the airway body 21, an air pressure difference is formed inside the vaporization suction nozzle, so that under the action of the air pressure difference, air entering through the first air inlet channel 12 is adhered to the inner wall of the air guide channel 112 and forms blocking airflows on the inner wall of the air guide channel 112 to block the vapor and the inner wall of the air guide channel 112, thereby reducing condensate formed by the vapor on the inner wall of the air guide channel 112. When inhaling is not performed on the vaporization suction nozzle, there is no air pressure difference inside the vaporization suction nozzle, and there is no blocking airflow formed on the inner wall of the air guide channel 112.

Further, a flow direction of the blocking airflows is parallel to the inner wall of the airflow channel 11, that is, the flow direction of the blocking airflows is parallel to the inner wall of the air guide channel 112, and to be specific, the flow direction of the blocking airflows is parallel to the inner wall of the tube body 22, to ensure a desirable effect of the blocking airflows for blocking the vapor and the inner wall of the tube body 22.

Optionally, to enable the blocking airflows to be adhered to the inner wall of the air guide channel 112 to form an air curtain. In a specific embodiment, there may be a plurality of first air inlet channels 12, and the plurality of first air inlet channels 12 are spaced in a circumferential direction of the wall portion 211.

Figure 3:
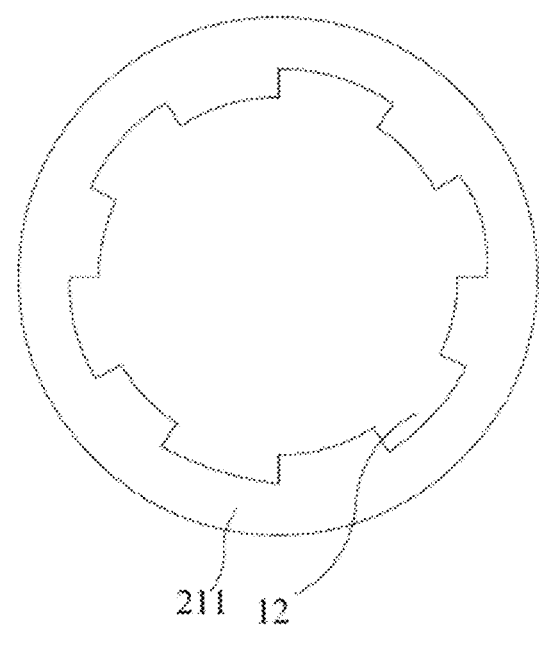
FIG. 3 is a schematic structural diagram of first air inlet channels of an airway body of a vaporization suction nozzle according to this application.

Referring to FIG. 3 together, FIG. 3 is a schematic structural diagram of first air inlet channels of an airway body of a vaporization suction nozzle according to this application. The airway body 21 includes a wall portion 211 covering the air guide channel 112. The first air inlet channel 12 is located on the wall portion 211 and is in communication with the air guide channel 112. As shown in FIG. 3, there are a plurality of first air inlet channels 12 evenly provided along the wall portion 211 in a circumferential direction. In a specific embodiment, the shape of the first air inlet channels 12 is not limited as long as air can flow into the air guide channel 112 through the first air inlet channels 12 during inhaling. In an optional embodiment, the shape of the first air inlet channels 12 may be any one of or any combination of a square, a circle, or a triangle.

Further, the size of the first air inlet channels 12 is to be appropriately set when the first air inlet channels 12 are provided, so that air entering through the first air inlet channels 12 can form blocking airflows completely covering the inner wall of the air guide channel 112 on the inner wall of the air guide channel 112.

Still referring to FIG. 1, the airway body 21 of the vaporization suction nozzle in this application includes a first airway portion 212, a second airway portion 213, and the wall portion 211 connecting the first airway portion 212 to the second airway portion 213 and covering a part of the air guide channel 112. The entrance channel 111 is mainly located in the first airway portion 212 and is in communication with the air guide channel 112, and the second airway portion 213 is sleeved on an outer side of the tube body 22 of the suction nozzle portion. In a specific embodiment, the wall portion 211 abuts against one end of the air guide channel 112. In another embodiment, there may alternatively a gap between the wall portion 211 and one end of the air guide channel 112 as long as it can be ensured that vapor leakage will not occur.

Optionally, still referring to FIG. 2, the first airway portion 212 further includes a vent portion 214 and a first connection portion 215, where the first connection portion 215 is located on one side of the wall portion 211 away from the second airway portion 213, and the vent portion 214 is located on one side of the first connection portion 215 away from the wall portion 211. A cross-sectional area (where the cross section is defined as a section perpendicular to an axial direction, similarly hereinafter) of the first connection portion 215 is less than a cross-sectional area of the vent portion 214. A clamping opening 216 is formed at a position where the first connection portion 215 is connected to the vent portion 214, and the clamping opening 216 is configured to clamp a vapor generation device (which is a part of the electronic vaporization device for generating vapor, not shown in the figure). Further, referring to FIG. 1 and FIG. 2, a comprehensive airway 14 is formed at a position where the clamping opening 216 is located, so that air flows into the first air inlet channels 12 through the comprehensive airway 14 and then flows into the air guide channel 112 through the first air inlet channels 12. During inhaling, after the air pressure difference is generated, blocking airflows are formed on the inner wall of the air guide channel 112 under the action of the air pressure difference. The blocking airflows block the vapor and the air guide channel 112, thereby reducing condensate formed by the vapor in the air guide channel 112.

Optionally, in an implementation, the first airway portion 212, the second airway portion 213, and the wall portion 211 connecting the first airway portion 212 to the second airway portion 213 of the airway body 21 are integrally formed. In another implementation, the first airway portion 212, the second airway portion 213, and the wall portion 211 connecting the first airway portion 212 to the second airway portion 213 of the airway body 21 may also be formed through a welding process.

Optionally, the second airway portion 213 of the airway body 21 is sleeved on the outer side of the tube body 22 of the suction nozzle portion. Specifically, in an implementation, the airway body 21 and the tube body 22 may be designed to be integrally formed. In another implementation, the second airway portion 213 may alternatively be sleeved on the outer side of the tube body 22 of the suction nozzle portion in a matching manner. To avoid vapor leakage, the second airway portion 213 may be sleeved on the outer side of the tube body 22 of the suction nozzle portion in an interference-fitting manner.

In the vaporization suction nozzle provided in this embodiment, the first air inlet channels 12 in communication with the air guide channel 112 are provided on the wall portion 211 that covers the air guide channel 112. When an inhaling action is performed on the tube body 22 and the vapor simultaneously flows into the air guide channel 112 through the entrance channel 111, air flows into the air guide channel 112 through the first air inlet channels 12, and the air entering through the first air inlet channels 12 may form blocking airflows on the inner wall of the air guide channel 112 under the action of the air pressure, to block the vapor and the inner wall of the air guide channel 112, thereby preventing the vapor from forming condensate on the inner wall of the air guide channel 112.

Figure 4:
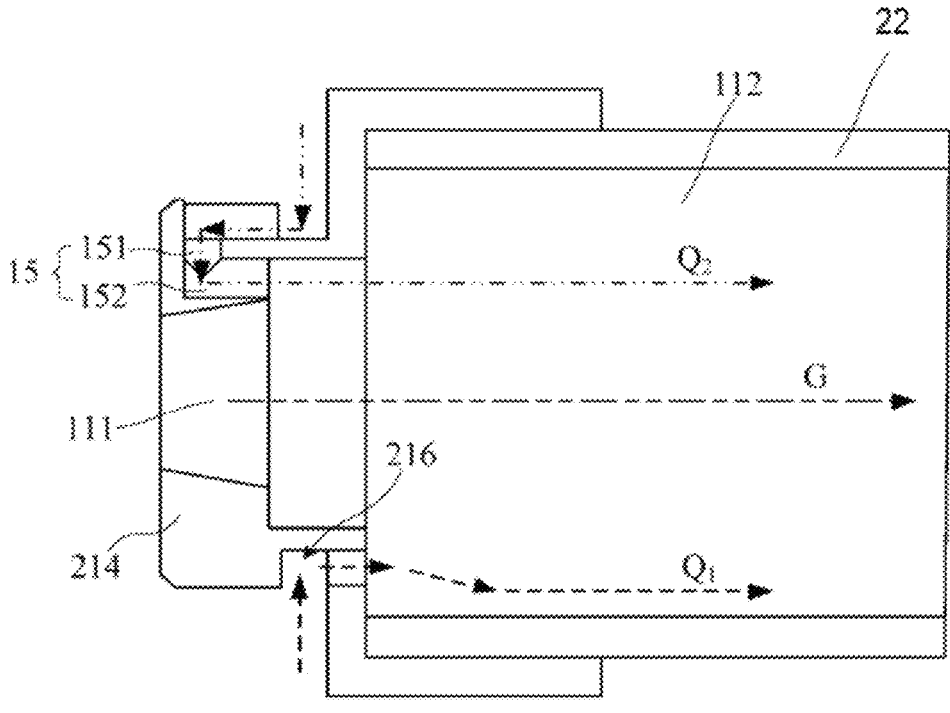
FIG. 4 is a schematic structural diagram of a second embodiment of a vaporization suction nozzle according to this application.

Referring to FIG. 4, FIG. 4 is a schematic structural diagram of a second embodiment of a vaporization suction nozzle according to this application. Compared with the first embodiment shown in FIG. 1, the difference between the first embodiment and the second embodiment is that: in this embodiment, second air inlet channels 15 are provided on an outer side of the vent portion 214. The second air inlet channels 15 are configured to increase a speed of discharging the vapor, to further prevent the vapor from forming condensate on the inner wall of the air guide channel 112.

Optionally, the second air inlet channel 15 includes an air inlet portion 151 and an air guide portion 152. Specifically, the air inlet portion 151 is arranged surrounding the vent portion 214 in a direction parallel to the wall portion 211, an extending direction of the air guide portion 152 is arranged parallel to an extending direction of the entrance channel 111, and the air guide portion 152 is connected to an end of the air inlet portion 151 that is located in the vent portion 214. Air enters through the air inlet portion 151 and flows into the air guide channel 112 through the air guide portion 152.

Figure 5:
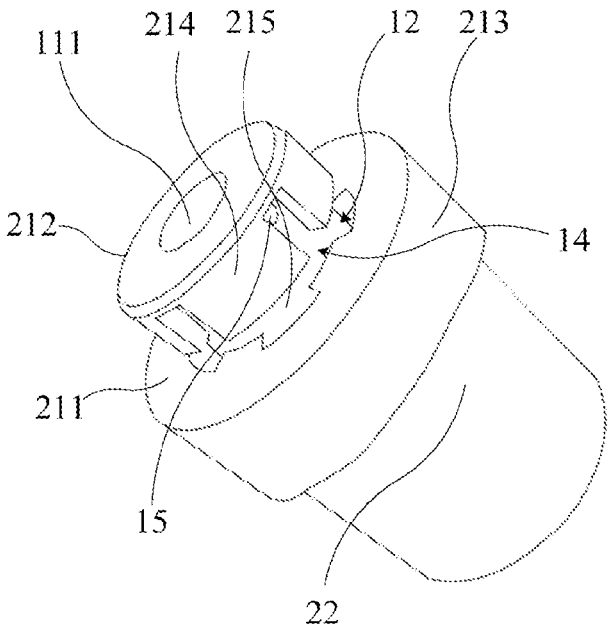
FIG. 5 is a schematic three-dimensional structural diagram of a second embodiment of a vaporization suction nozzle according to this application.
Figure 6:
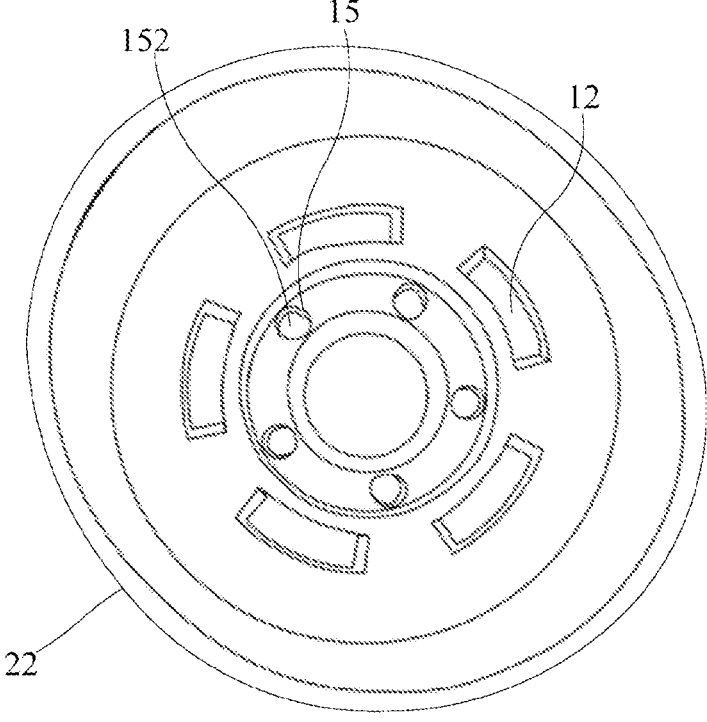
FIG. 6 is a schematic bottom structural diagram of a second embodiment of a vaporization suction nozzle according to this application.

Optionally, referring to FIG. 4 and FIG. 5, FIG. 5 is a schematic three-dimensional structural diagram of a second embodiment of a vaporization suction nozzle according to this application. The second air inlet channels 15 are located in the vent portion 214, and the first air inlet channels 12 are located on the wall portion 211 that connects the first airway portion 212 to the second airway portion 213. In a specific embodiment, when the tube body 22 of the suction nozzle portion generates an inhaling force, the vapor enters through the entrance channel 111, and air enters through the second air inlet channels 15 and the first air inlet channels 12. Referring to FIG. 6, FIG. 6 is a schematic bottom structural diagram of a second embodiment of a vaporization suction nozzle according to this application. As shown in FIG. 6, the first air inlet channels 12 are closer to the inner wall of the tube body 22 relative to the air guide portions 152 in the second air inlet channels 15. Therefore, during inhaling, air enters through the first air inlet channels 12 and forms blocking airflows on the inner wall of the air guide channel of the tube body 22 of the suction nozzle portion under the action of the air pressure, to block the vapor entering through the entrance channel 111 and the inner wall of the air guide channel, and reducing condensate formed by the vapor on the inner wall of the air guide channel. Further, the second air inlet channels 15 are provided, air flows into the second air inlet channels 15 during inhaling, and the air increases the speed of discharging the vapor entering through the entrance channel 111 from the air guide channel 112, thereby further preventing the vapor from forming condensate on the inner wall of the air guide channel.

Further, still referring to FIG. 4 and FIG. 5, a clamping opening 216 is formed at a position where the first connection portion 215 is connected to the vent portion 214, and the clamping opening 216 is configured to clamp a vapor generation device (not shown in the figure). Further, a comprehensive airway 14 is formed at a position where the clamping opening 216 is located, so that air flows into the first air inlet channels 12 and the second air inlet channels 15 through the comprehensive airway 14 and then flows into the air guide channel 112 through the first air inlet channels 12. During inhaling, after the air pressure difference is generated, blocking airflows are formed on the inner wall of the air guide channel 112 under the action of the air pressure difference. As shown in FIG. 4, the blocking airflow (as shown by an arrow Q1 in FIG. 4) blocks the vapor (as shown by an arrow G in FIG. 4) and the air guide channel 112, thereby reducing condensate formed by the vapor on the inner wall of the air guide channel 112. Air flows into the air guide portions 152 through the second air inlet channels 15 and forms a second airflow after flowing into the air guide channel 112. The second airflow increases the speed of discharging the vapor.

Optionally, in this embodiment, the shape of the air guide portion 152 of the second air inlet channel 15 may be any one of or any combination of a square, a circle, or a triangle. The shape of the air inlet portion 151 of the second air inlet channel 15 may alternatively be any one of or any combination of a square, a circle, or a triangle, which is not specifically limited as long as air can be introduced into the air guide portion 152 and then flow into the air guide channel 112.

In an embodiment, there is at least one second air inlet channel 15 circumferentially provided on an outer side of the vent portion 214.

In an embodiment, the first air inlet channels 15 may be provided corresponding to the second air inlet channels 12. In another embodiment, the second air inlet channels 15 and the first air inlet channels 12 may also be staggered. Specifically, to reduce the mutual impact between airflows formed by air flowing into the first air inlet channels 12 and the second air inlet channels 15, the second air inlet channels 15 and the first air inlet channels 12 are staggered, as shown in FIG. 6.

In an embodiment, when the first air inlet channels 12 and the second air inlet channels 15 are provided, there is a speed difference between the airflows formed in the second air inlet channels 15 and the first air inlet channels 12, to ensure that air entering through the first air inlet channels 12 forms blocking airflows on the inner wall of the air guide channel 112, which can block the vapor and the air guide channel 112, and air entering through the second air inlet channels 15 can increase the speed of discharging the vapor. In a specific embodiment, a flow rate of the airflows formed in the first air inlet channels 12 is greater than a flow rate of the airflows formed in the second air inlet channels 15, thereby weakening the impact on a deliver direction of the vapor while achieving the effect of reducing the condensate.

Specifically, the flow rates of the airflows formed in the first air inlet channel 12 and the second air inlet channel 15 are related to the size of the opening. To be specific, a larger size of the opening indicates a faster flow rate. Therefore, in a specific implementation, to realize that the flow rate of the airflow formed in the first air inlet channel 12 is greater than the flow rate of the airflow formed in the second air inlet channel 15, a size of the first air inlet channel 12 (that is, a cross-sectional area, where a cross section of the first air inlet channel 12 should be a section taken perpendicular to an extending direction of the first air inlet channel 12) is set to be greater than a size of the second air inlet channel 15 (that is, a cross-sectional area, where a cross section of the second air inlet channel 15 should be a section taken perpendicular to an extending direction of the second air inlet channel 15). Alternatively, in another embodiment, a quantity of the first air inlet channels 12 is greater than a quantity of the second air inlet channels 15.

As shown in FIG. 4, when an air pressure difference is generated because a user inhales, under the action of the air pressure difference, an external airflow flows into the airflow channel 11 (that is, the air guide channel 112) through the first air inlet channel 12 and then forms a blocking airflow Q1 on the inner wall of the airflow channel 11. The blocking airflow Q1 blocks vapor G and the inner wall of the airflow channel 11, to reduce condensate formed by the vapor G on the inner wall of the airflow channel 11. In addition, an airflow Q2 flowing into the airflow channel 11 through the second air inlet channel 15 flows along an outer edge of the vapor G under the action of the air pressure difference, to increase the speed of discharging the vapor G.

Figure 7:
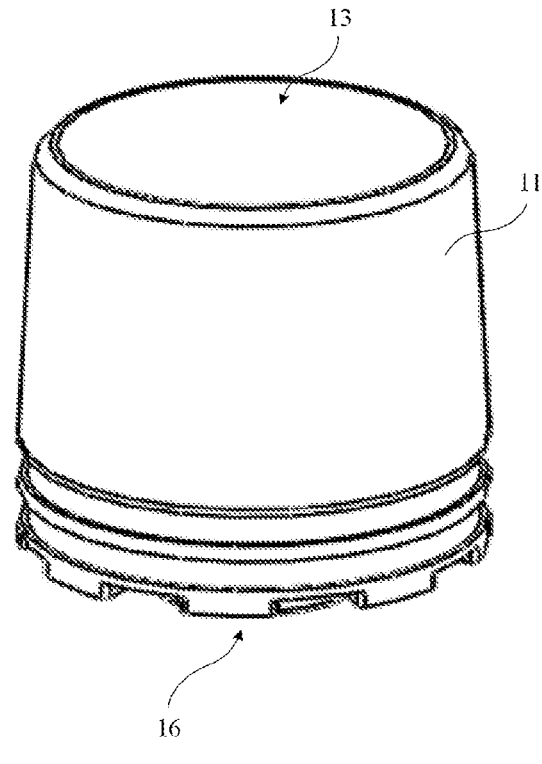
FIG. 7 is a schematic structural diagram of a third embodiment of a vaporization suction nozzle according to this application.
Figure 8:
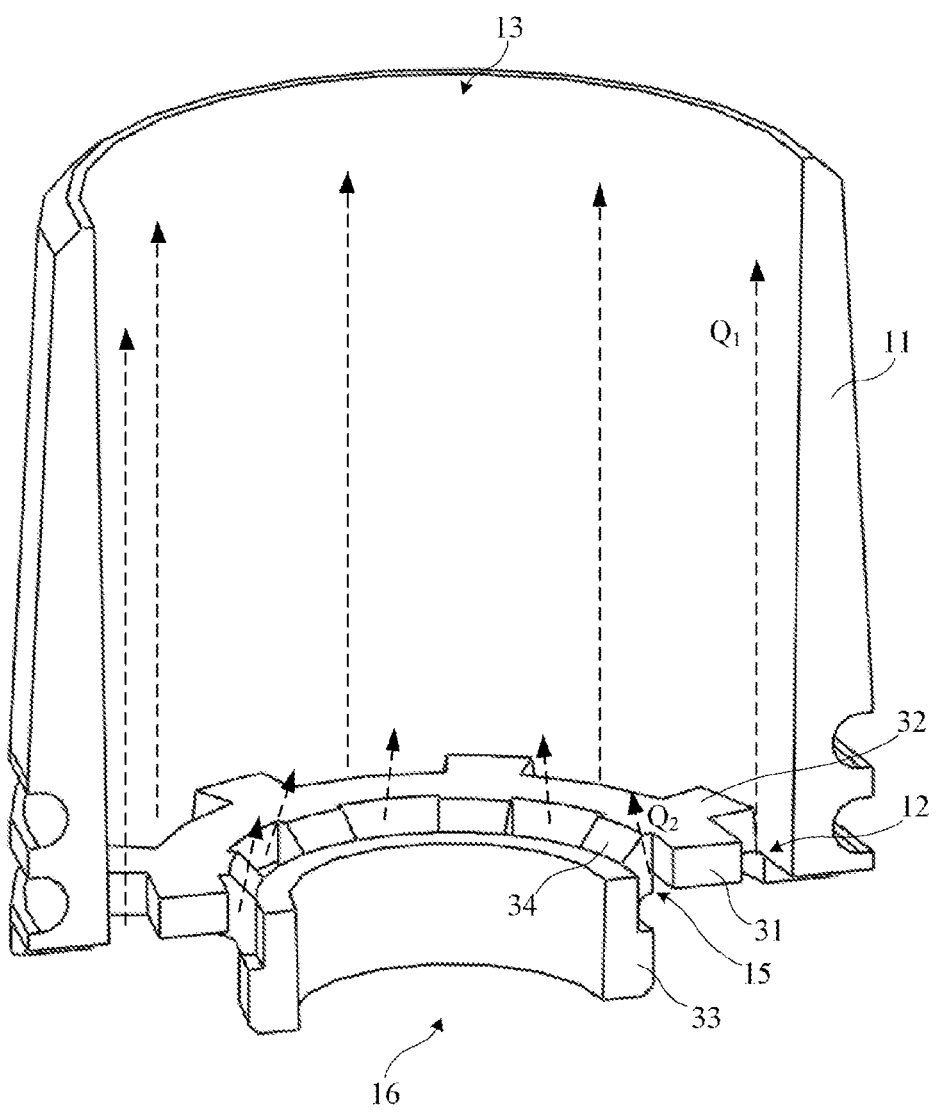
FIG. 8 is a schematic cross-sectional structural diagram of a third embodiment of a vaporization suction nozzle according to this application.

Referring to FIG. 7 and FIG. 8, FIG. 7 is a schematic structural diagram of a third embodiment of a vaporization suction nozzle according to this application, and FIG. 8 is a schematic cross-sectional structural diagram of a third embodiment of a vaporization suction nozzle according to this application.

An exemplary embodiment in which the air-curtain forming structure is a vaporization suction nozzle applicable to the electronic vaporization device is described below.

In this embodiment, the air-curtain forming structure is in a form of the vaporization suction nozzle. The vaporization suction nozzle provided in this embodiment is applicable to electronic vaporization devices such as an e-cigarette and a medical vaporization suction nozzle.

Specifically, the vaporization suction nozzle includes an airflow channel 11. The airflow channel 11 is configured to deliver vapor. The vaporization suction nozzle further includes first air inlet channels 12 in communication with the airflow channel 11, and the first air inlet channels 12 are configured to introduce external airflows into the airflow channel 11, so that blocking airflows (as shown by arrows Q1 in FIG. 8, similarly hereinafter) are formed between the inner wall of the airflow channel 11 and the vapor. The blocking airflows form an air curtain.

Further, the vaporization suction nozzle further includes a first air inlet 16 and an air outlet 13. The first air inlet 16 and the air outlet 13 are provided opposite to each other and respectively in communication with the airflow channel 11. Vapor flows into the airflow channel 11 through the first air inlet 16 and is delivered to the air outlet 13 through the airflow channel 11, and then the vapor is outputted from the air outlet 13 for the user to inhale. The first air inlet channels 12 are close to the inner wall of the airflow channel 11, and exits of the first air inlet channels 12 face the air outlet 13, to ensure that the airflows flowing into the airflow channel 11 through the first air inlet channels 12 can flow along the inner wall of the airflow channel 11 (that is, an inner wall of the vaporization suction nozzle), that is, the blocking airflows (as shown by arrows Q1 in FIG. 8, similarly hereinafter) are formed to block the vapor and the inner wall of the airflow channel 11, that is, block the vapor and the inner wall of the vaporization suction nozzle, so that the vapor may be in contact with the inner wall of the vaporization suction nozzle as little as possible, thereby alleviating the problem of vapor condensation and reducing condensate generation.

Further, a flow direction of the blocking airflows is parallel to the inner wall of the airflow channel 11, that is, the flow direction of the blocking airflows is parallel to the inner wall of the vaporization suction nozzle, to ensure a desirable effect of the blocking airflows for blocking the vapor and the inner wall of the vaporization suction nozzle.

In an embodiment, still referring to FIG. 8, the vaporization suction nozzle further includes a first airflow guide portion 31. The first air inlet channels 12 are formed between the first airflow guide portion 31 and the inner wall of the airflow channel 11, and the first airflow guide portion 31 is configured to guide airflows introduced through the first air inlet channels 12 to flow along the inner wall of the airflow channel 11, to form the blocking airflows.

Further, the vaporization suction nozzle further includes a second connection portion 32. The first airflow guide portion 31 is connected to the inner wall of the airflow channel 11 through the second connection portion 32.

Figure 9:
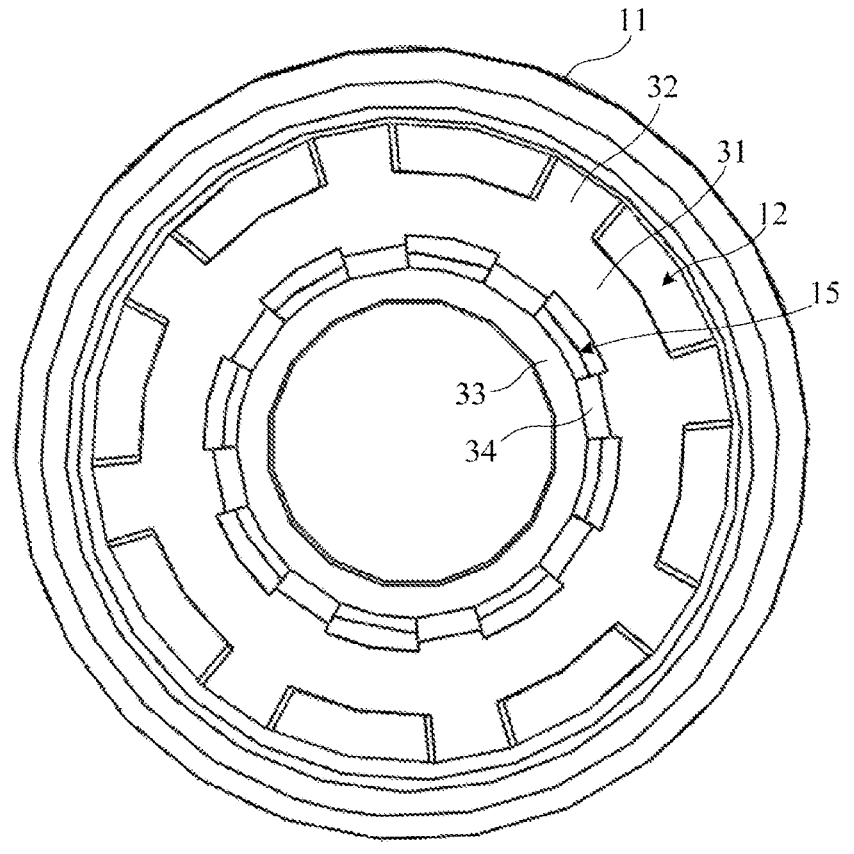
FIG. 9 is a schematic top structural diagram of a third embodiment of a vaporization suction nozzle according to this application.

Specifically, referring to FIG. 9 together, a plurality of second connection portions 32 are arranged between the first airflow guide portion 31 and the inner wall of the airflow channel 11. The plurality of second connection portions 32 are spaced in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channels 12 between the first airflow guide portion 31 and the inner wall of the airflow channel 11 is ensured.

Further, a plurality of first air inlet channels 12 can be formed between the first airflow guide portion 31 and the inner wall of the airflow channel 11, blocking airflows formed by the plurality of first air inlet channels 12 form an air curtain, as shown in FIG. 8, which greatly enables vapor to be in contact with the inner wall of the vaporization suction nozzle (that is, the inner wall of the airflow channel 11) as little as possible, and the problem of vapor condensation can be alleviated, thereby reducing condensate generation.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 8, the vaporization suction nozzle further includes a second airflow guide portion 33. The second airflow guide portion 33 is away from the inner wall of the airflow channel 11 relative to the first airflow guide portion 31, the second air inlet channels 15 are formed between the second airflow guide portion 33 and the first airflow guide portion 31, the exits of the second air inlet channels 15 face the air outlet 13, and airflows (as shown by arrows Q2 in FIG. 8) entering through the second air inlet channels 15 are used to guide the vapor to be outputted from the air outlet 13, thereby speeding up the discharge of the vapor.

Further, the second airflow guide portion 33 is annularly arranged to surround the first air inlet 16 of the vaporization suction nozzle.

Further, the air-curtain forming structure further includes a third connection portion 34, and the second airflow guide portion 33 is connected to the first airflow guide portion 31 through the third connection portion 34, so that a relative position of the second airflow guide portion 33 in the vaporization suction nozzle is fixed through the first airflow guide portion 31.

Specifically, referring to FIG. 9 together, a plurality of third connection portions 34 are arranged between the second airflow guide portion 33 and the first airflow guide portion 31, the plurality of third connection portions 34 are sequentially spaced in a circumferential direction of the second airflow guide portion 33, and the second air inlet channels 15 are formed between adjacent third connection portions 34. In this way, the relative position of the second airflow guide portion 33 in the vaporization suction nozzle is fixed, and formation of the second air inlet channels 15 between the second airflow guide portion 33 and the first airflow guide portion 31 is ensured.

Figure 10:
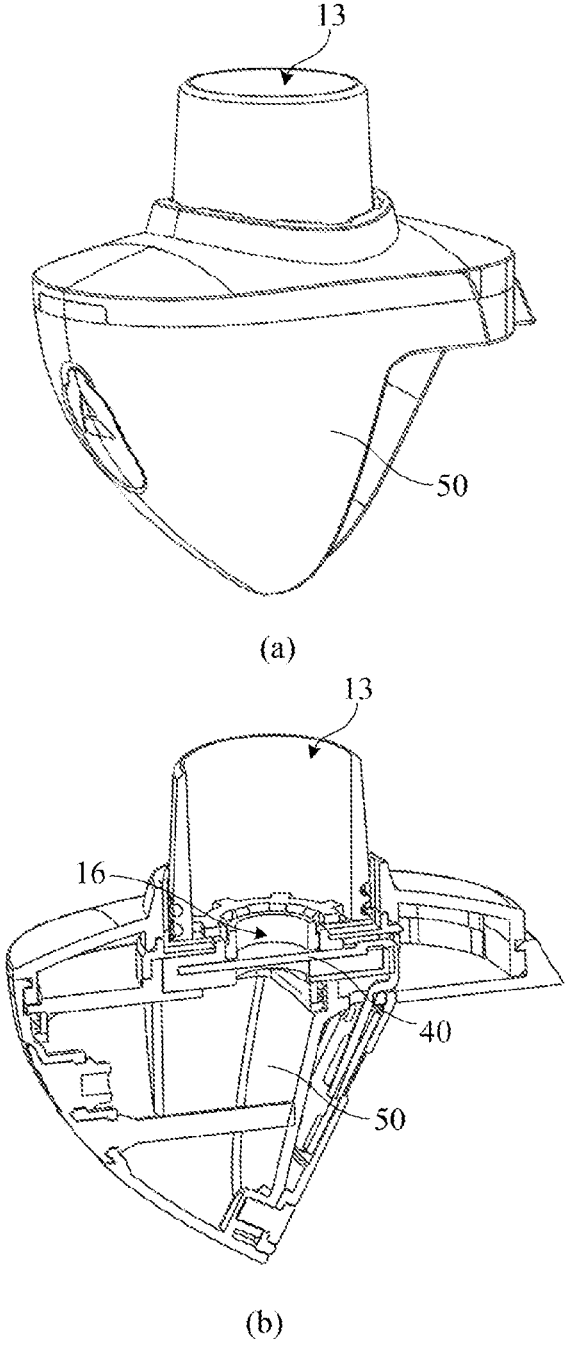
FIG. 10 is a schematic structural diagram of a first embodiment of a vaporizer according to this application.
Figure 11:
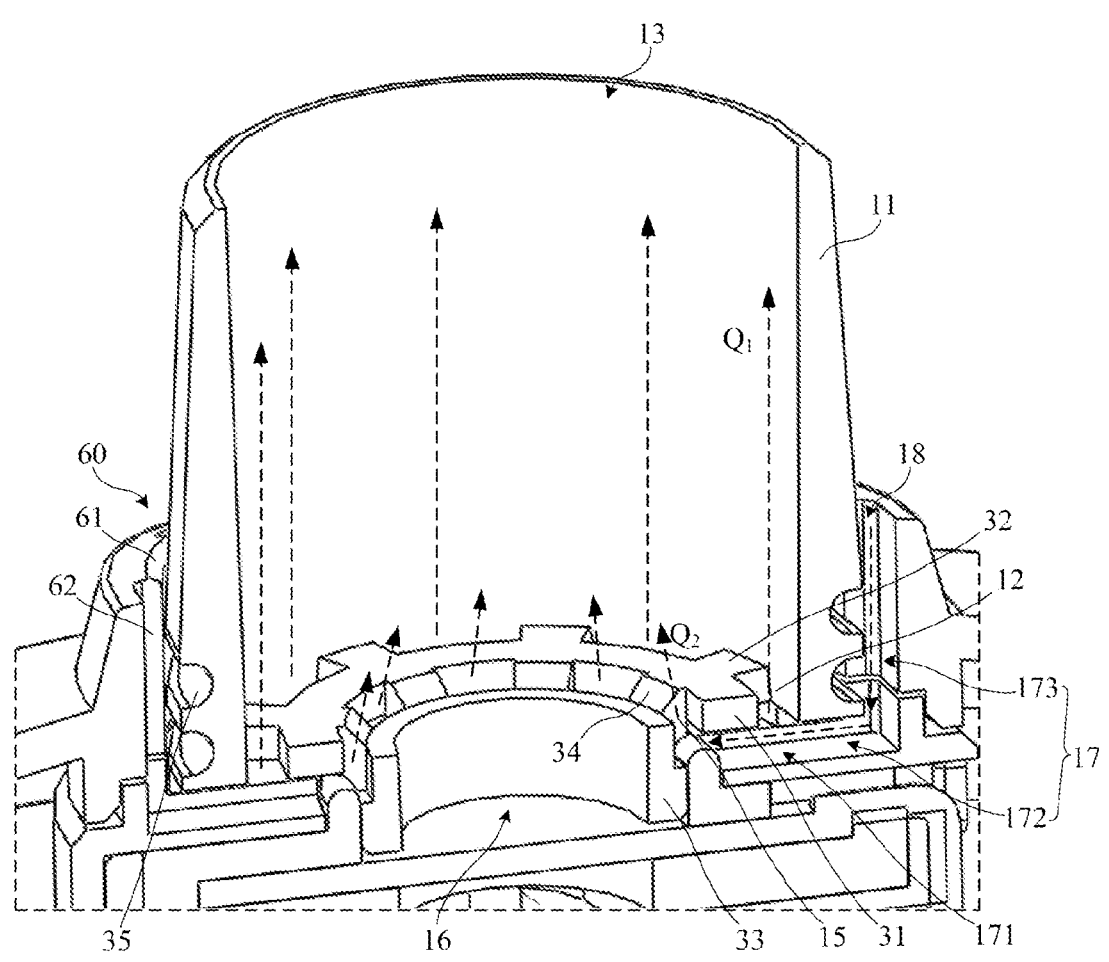
FIG. 11 is a schematic partial cross-sectional structural diagram of a first embodiment of a vaporizer according to this application.

Referring to FIG. 10 and FIG. 11, FIG. 10 is a schematic structural diagram of a first embodiment of a vaporizer according to this application, and FIG. 11 is a schematic partial cross-sectional structural diagram of a first embodiment of a vaporizer according to this application.

An exemplary embodiment in which the air-curtain forming structure is a vaporizer applicable to the electronic vaporization device is described below.

In this embodiment, the air-curtain forming structure is in a form of the vaporizer. The vaporizer provided in this embodiment is applicable to electronic vaporization devices such as an e-cigarette and a medical vaporizer. FIG. 10 shows a case in which the air-curtain forming structure is applicable to the medical vaporizer, which is merely used for description and is not intended to limit an application environment of the air-curtain forming structure in this embodiment.

In this embodiment, referring to FIG. 10, the air-curtain forming structure includes a vaporization suction nozzle, a vaporization core 40, and a liquid storage cavity 50. The vaporization suction nozzle includes a first air inlet 16 and an air outlet 13, vapor flows into the vaporization suction nozzle through the first air inlet 16 and is delivered to the air outlet 13 through the vaporization suction nozzle, and then the vapor is outputted from the air outlet 13 for the user to inhale. The vaporization core 40 is arranged at a position where the first air inlet 16 of the vaporization suction nozzle is located and is configured to vaporize an aerosol generation substrate stored in the liquid storage cavity 50 to generate vapor.

The vapor generation device of the air-curtain forming structure in this embodiment includes structures such as the vaporization core 40 and the liquid storage cavity 50, and is configured to generate vapor.

For the case in which the air-curtain forming structure in this embodiment is applicable to the medical vaporizer, the vaporization core 40 may be an ultrasonic vaporization sheet, and the ultrasonic vaporization sheet vaporizes the aerosol generation substrate through high-frequency oscillation. The specific principle thereof falls within the understanding scope of a person skilled in the art, and details are not described herein again. Certainly, for the case in which the air-curtain forming structure is applied to other fields, the vaporization core 40 may also generate vapor in a manner of heating and vaporizing the aerosol generation substrate, which is not limited herein.

Specifically, still referring to FIG. 11, the vaporization suction nozzle includes an airflow channel 11. The airflow channel 11 is configured to deliver vapor. The vaporization suction nozzle further includes first air inlet channels 12 in communication with the airflow channel 11, and the first air inlet channels 12 are configured to introduce external airflows into the airflow channel 11, so that blocking airflows (as shown by arrows Q1 in FIG. 11, similarly hereinafter) are formed between the inner wall of the airflow channel 11 and the vapor. The blocking airflows form an air curtain.

Further, the first air inlet 16 and the air outlet 13 are provided opposite to each other and are respectively in communication with the airflow channel 11. The first air inlet channels 12 are close to the inner wall of the airflow channel 11, and exits of the first air inlet channels 12 face the air outlet 13, to ensure that the airflows flowing into the airflow channel 11 through the first air inlet channels 12 can flow along the inner wall of the airflow channel 11 (that is, an inner wall of the vaporization suction nozzle), that is, the blocking airflows are formed to block the vapor and the inner wall of the airflow channel 11, that is, block the vapor and the inner wall of the vaporization suction nozzle, so that the vapor may be in contact with the inner wall of the vaporization suction nozzle as little as possible, thereby alleviating the problem of vapor condensation and reducing condensate generation.

Further, a flow direction of the blocking airflows is parallel to the inner wall of the airflow channel 11, that is, the flow direction of the blocking airflows is parallel to the inner wall of the vaporization suction nozzle, to ensure a desirable effect of the blocking airflows for blocking the vapor and the inner wall of the vaporization suction nozzle. In an embodiment, still referring to FIG. 11, the vaporization suction nozzle further includes a first airflow guide portion 31. The first air inlet channels 12 are formed between the first airflow guide portion 31 and the inner wall of the airflow channel 11, and the first airflow guide portion 31 is configured to guide airflows introduced through the first air inlet channels 12 to flow along the inner wall of the airflow channel 11, to form the blocking airflows.

Further, the vaporization suction nozzle further includes a second connection portion 32. The first airflow guide portion 31 is connected to the inner wall of the airflow channel 11 through the second connection portion 32.

Specifically, a plurality of second connection portions 32 are arranged between the first airflow guide portion 31 and the inner wall of the airflow channel 11. The plurality of second connection portions 32 are spaced in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channels 12 between the first airflow guide portion 31 and the inner wall of the airflow channel 11 is ensured.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 11, the vaporization suction nozzle further includes a second airflow guide portion 33. The second airflow guide portion 33 is away from the inner wall of the airflow channel 11 relative to the first airflow guide portion 31, the second air inlet channels 15 are formed between the second airflow guide portion 33 and the first airflow guide portion 31, the exits of the second air inlet channels 15 face the air outlet 13, and airflows entering through the second air inlet channels 15 are used to guide the vapor to be outputted from the air outlet 13, thereby speeding up the discharge of the vapor.

Further, the second airflow guide portion 33 is annularly arranged to surround the first air inlet 16 of the vaporization suction nozzle.

Further, the air-curtain forming structure further includes a third connection portion 34, and the second airflow guide portion 33 is connected to the first airflow guide portion 31 through the third connection portion 34, so that a relative position of the second airflow guide portion 33 in the vaporization suction nozzle is fixed through the first airflow guide portion 31.

Specifically, a plurality of third connection portions 34 are arranged between the second airflow guide portion 33 and the first airflow guide portion 31, the plurality of third connection portions 34 are sequentially spaced in a circumferential direction of the second airflow guide portion 33, and the second air inlet channels 15 are formed between adjacent third connection portions 34. In this way, the relative position of the second airflow guide portion 33 in the vaporization suction nozzle is fixed, and formation of the second air inlet channels 15 between the second airflow guide portion 33 and the first airflow guide portion 31 is ensured.

In an embodiment, still referring to FIG. 11, the air-curtain forming structure further includes a converging channel 17, one end of the converging channel 17 is an air inlet, that is, a second air inlet 18, and the other end of the converging channel 17 is a diverging opening 171, where the diverging opening 171 is respectively in communication with the first air inlet channels 12 and the second air inlet channels 15.

Specifically, the converging channel 17 includes a first channel section 172 and a second channel section 173 that are in communication with each other, an end opening of the first channel section 172 away from the second channel section 173 is the diverging opening 171, and an end opening of the second channel section 173 away from the first channel section 172 is the air inlet, that is, the second air inlet 18. An extending direction of the first channel section 172 is different from an extending direction of the second channel section 173.

FIG. 11 shows that the extending direction of the first channel section 172 is a horizontal direction, the extending direction of the second channel section 173 is a vertical direction, and the second channel section 173 extends toward the air outlet 13. When the user inhales, an external airflow flows into the second channel section 173 through the second air inlet 18 and is delivered into the first channel section 172, and then the airflow passes through the diverging opening 171 and flows into the airflow channel 11 in the vaporization suction nozzle respectively through the first air inlet channels 12 and the second air inlet channels 15, where flow conditions of airflows are shown by dashed arrows in FIG. 11.

Further, the air-curtain forming structure includes a mounting portion 60. The mounting portion 60 includes a mounting protrusion 61 and a vent groove 62, where the mounting protrusion 61 is configured to fix the vaporization suction nozzle. After the vaporization suction nozzle is fixed to the mounting portion 60, the first channel section 172 is formed between the vaporization suction nozzle and the mounting portion 60, and to be specific, the first channel section 172 is formed between the vaporization suction nozzle and the bottom of the mounting portion 60. In addition, the second channel section 173 is formed between the vent groove 62 and the vaporization suction nozzle.

In an embodiment, still referring to FIG. 11, the periphery of the vaporization suction nozzle is provided with limiting grooves 35 surrounding in a circumferential direction thereof, where the limiting grooves 35 are configured to place elastic rings to fix the vaporization suction nozzle. Specifically, after the vaporization suction nozzle is embedded in the mounting portion 60 mentioned above, the elastic rings placed in the limiting grooves 35 are in elastically interference fit with the mounting protrusion 61 in the mounting portion 60, to fix the vaporization suction nozzle in the mounting portion 60.

It is to be noted that, the elastic ring located at a position where the vent groove 62 in the mounting portion 60 is located may not block a gap between the vaporization suction nozzle and the vent groove 62, to ensure a ventilation function between the vaporization suction nozzle and the vent groove 62, thereby ensuring that the external airflows can flow into the airflow channel 11 to form blocking airflows and speed up the discharge of the vapor.

Optionally, there may be a plurality of limiting grooves 35, where the plurality of limiting grooves 35 are spaced in an axial direction of the vaporization suction nozzle. By designing a plurality of limiting grooves 35, the sufficient bonding strength between the vaporization suction nozzle and the mounting portion 60 can be ensured, to prevent the vaporization suction nozzle from falling off. In addition, the elastic ring may be a silicone ring, which is not limited herein.

Figure 12:
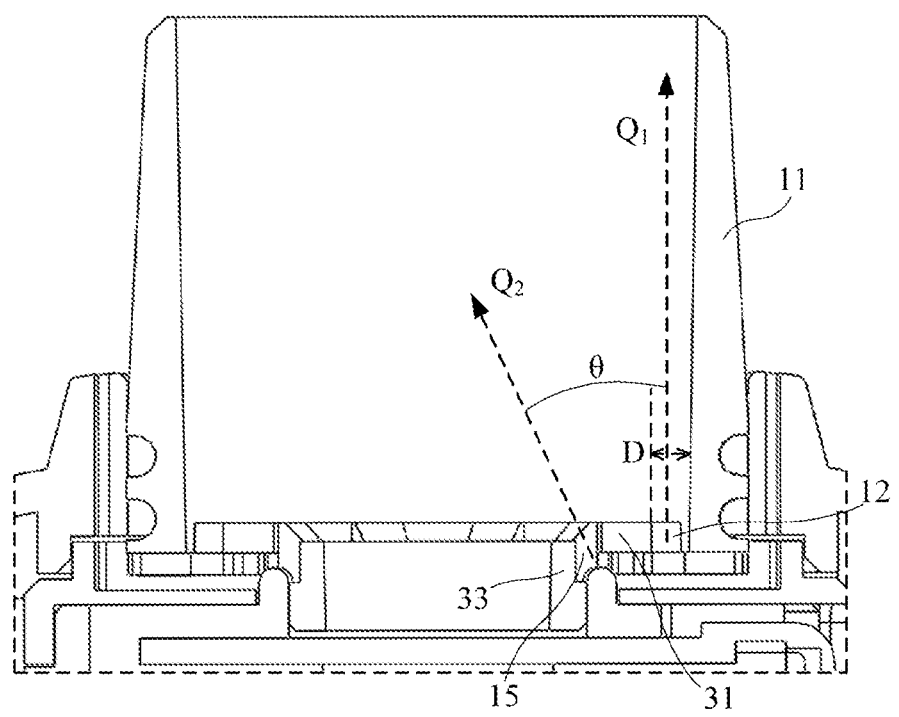
FIG. 12 is a schematic partial cross-sectional structural diagram of a first embodiment of a vaporizer from another perspective according to this application.

Referring to FIG. 12, FIG. 12 is a schematic partial cross-sectional structural diagram of a first embodiment of a vaporizer from another perspective according to this application. Airflow conditions in the first air inlet channel 12 and the second air inlet channel 15 in this exemplary embodiment are described below.

According to an aspect, a cross-sectional area of the first air inlet channel 12 may affect an amount of the blocking airflows. Specifically, in a case that the air pressure difference caused by user inhaling is fixed, within a specific range, a larger cross-sectional area of the first air inlet channel 12 indicates a larger amount of the blocking airflows. To be specific, a larger distance D between the first airflow guide portion 31 and the inner wall of the vaporization suction nozzle (that is, the inner wall of the airflow channel 11) indicates a larger cross-sectional area of the first air inlet channel 12 and a larger amount of the blocking airflows.

It may be understood that, since the air pressure difference caused by user inhaling is limited, there is an upper limit on the amount of the blocking airflows. When the amount of the blocking airflows reaches the upper limit, the amount of the blocking airflows may not significantly increase even if the distance between the first airflow guide portion 31 and the inner wall of the vaporization suction nozzle continues to be increased.

According to another aspect, a flow direction of an airflow (as shown by an arrow Q2 in FIG. 12, similarly hereinafter) flowing into the airflow channel 11 (that is, the vaporization suction nozzle) through the second air inlet channel 15 may affect airflow conditions in the airflow channel 11. Specifically, in a case that an angle (as shown by an angle θ in FIG. 12, similarly hereinafter) between the flow direction of the airflow entering through the second air inlet channel 15 and a preset direction is excessively small, the airflow entering through the second air inlet channel 15 is affected and drawn by the blocking airflow. As a result, the airflow entering through the second air inlet channel 15 cannot be outputted well carrying the vapor, and the effect of speeding up the discharge of the vapor is greatly weakened. In addition, in a case that the angle between the flow direction of the airflow entering through the second air inlet channel 15 and the preset direction is excessively large, the airflow entering through the second air inlet channel 15 may block an output path of the vapor, preventing the vapor from being delivered to the air outlet 13 of the vaporization suction nozzle. The preset direction is parallel to a flow direction of the blocking airflow (as shown by an arrow Q1 in FIG. 12), that is, the preset direction may be represented by the flow direction of the blocking airflow.

In view of this, the angle between the flow direction of the airflow entering through the second air inlet channel 15 and the preset direction preferably ranges from 30° to 45°, for example, 30°, 33°, 37°, 41°, 43°, 45°, or the like. In this way, it can be ensured that the airflow entering through the second air inlet channel 15 can be outputted carrying the vapor, to speed up the discharge of the vapor.

It is to be noted that, the flow direction of the airflow entering through the second air inlet channel 15 can be adjusted by adjusting the structure of the vaporization suction nozzle at a position where the second air inlet channel 15 is located. For example, the flow direction of the airflow entering through the second air inlet channel 15 can be adjusted by adjusting positions of the first airflow guide portion 31 and the second airflow guide portion 33 in an axial direction of the airflow channel 11, which is not limited herein.

Figure 13:
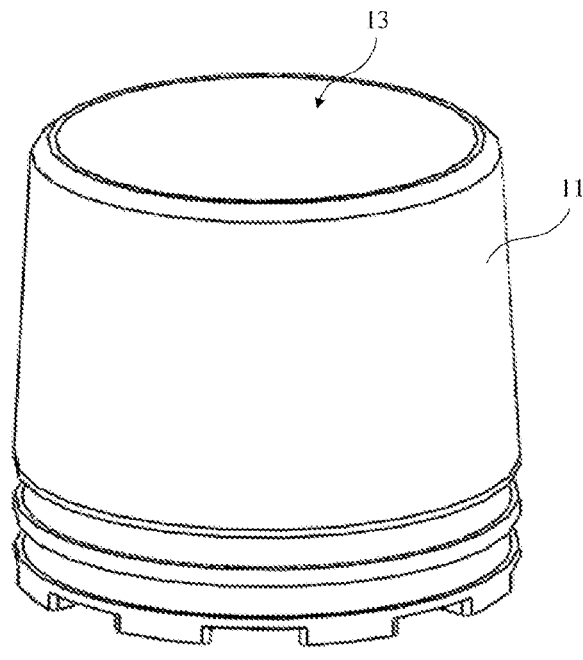
FIG. 13 is a schematic structural diagram of a fourth embodiment of a vaporization suction nozzle according to this application.
Figure 14:
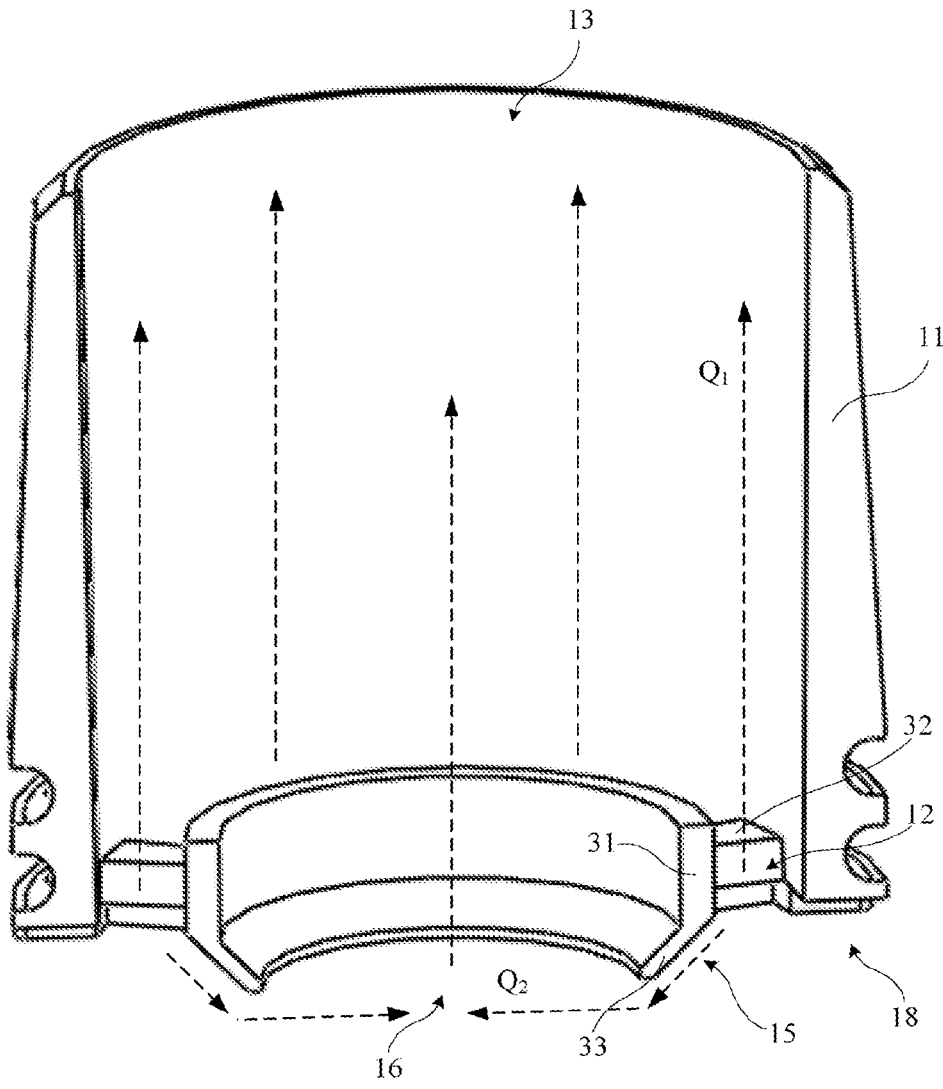
FIG. 14 is a schematic cross-sectional structural diagram of a fourth embodiment of a vaporization suction nozzle according to this application.

Referring to FIG. 13 and FIG. 14, FIG. 13 is a schematic structural diagram of a fourth embodiment of a vaporization suction nozzle according to this application, and FIG. 14 is a schematic cross-sectional structural diagram of a fourth embodiment of a vaporization suction nozzle according to this application.

An exemplary embodiment in which the air-curtain forming structure is a vaporization suction nozzle applicable to the electronic vaporization device is described below. The vaporization suction nozzle includes a first air inlet 16, a second air inlet 18, and an air outlet 13, where the first air inlet 16 and the air outlet 13 are provided opposite to each other. The vaporization suction nozzle further includes an airflow guide member. The airflow guide member is in communication with the second air inlet 18 and is configured to guide an airflow entering through the second air inlet 18 flows toward the first air inlet 16. Detailed descriptions are provided below.

In this embodiment, the air-curtain forming structure is in a form of the vaporization suction nozzle. The vaporization suction nozzle provided in this embodiment is applicable to electronic vaporization devices such as an e-cigarette and a medical vaporization suction nozzle.

Specifically, referring to FIG. 14, the vaporization suction nozzle includes an airflow channel 11. The airflow channel 11 is configured to deliver vapor. The vaporization suction nozzle further includes first air inlet channels 12 in communication with the airflow channel 11, and the first air inlet channels 12 are configured to introduce external airflows into the airflow channel 11, so that blocking airflows (as shown by arrows Q1 in FIG. 11, similarly hereinafter) are formed between the inner wall of the airflow channel 14 and the vapor. The blocking airflows form an air curtain.

Further, the vaporization suction nozzle further includes a first air inlet 16 and an air outlet 13. The first air inlet 16 and the air outlet 13 are provided opposite to each other and respectively in communication with the airflow channel 11. Vapor flows into the airflow channel 11 through the first air inlet 16 and is delivered to the air outlet 13 through the airflow channel 11, and then the vapor is outputted from the air outlet 13 for the user to inhale. The first air inlet channels 12 are close to the inner wall of the airflow channel 11, and exits of the first air inlet channels 12 face the air outlet 13, to ensure that the airflows flowing into the airflow channel 11 through the first air inlet channels 12 can flow along the inner wall of the airflow channel 11 (that is, an inner wall of the vaporization suction nozzle), that is, the blocking airflows are formed to block the vapor and the inner wall of the airflow channel 11, that is, block the vapor and the inner wall of the vaporization suction nozzle, so that the vapor may be in contact with the inner wall of the vaporization suction nozzle as little as possible, thereby alleviating the problem of vapor condensation and reducing condensate generation.

Further, a flow direction of the blocking airflows is parallel to the inner wall of the airflow channel 11, that is, the flow direction of the blocking airflows is parallel to the inner wall of the vaporization suction nozzle, to ensure a desirable effect of the blocking airflows for blocking the vapor and the inner wall of the vaporization suction nozzle.

In an embodiment, still referring to FIG. 14, the vaporization suction nozzle further includes the second air inlet 18 different from the first air inlet 16, where the second air inlet 18 is configured to guide an external airflow to flow into the vaporization suction nozzle. The vaporization suction nozzle further includes an airflow guide member. The airflow guide member is in communication with the second air inlet 18 and is configured to guide the airflow entering through the second air inlet 18 to flow toward the first air inlet 16, and then carry vapor flowing into the vaporization suction nozzle through the first air inlet 16 and output the vapor through the air outlet 13 of the vaporization suction nozzle, so that the user can inhale and the discharge of the vapor can be accelerated.

Specifically, at least a part of the airflow guide member is obliquely arranged in a direction away from the inner wall (that is, the inner wall of the airflow channel 11) and the air outlet 13 of the vaporization suction nozzle, to guide the airflow entering through the second air inlet 18 to flow toward the first air inlet 16, and further carry the vapor flowing into the vaporization suction nozzle through the first air inlet 16 and output the vapor through the air outlet 13 of the vaporization suction nozzle, so that the user can inhale and the discharge of the vapor can be accelerated.

In an embodiment, the airflow guide member includes a first airflow guide portion 31. The first air inlet channels 12 are formed between the first airflow guide portion 31 and the inner wall of the airflow channel 11 (that is, the inner wall of the vaporization suction nozzle), and are configured to guide airflows entering through the first air inlet channels 12 to flow along the inner wall of the airflow channel 11, where the airflows entering through the first air inlet channels 12 are used to form blocking airflows (as shown by arrows Q1 in FIG. 14, similarly hereinafter) between the inner wall of the vaporization suction nozzle and the vapor.

Further, the vaporization suction nozzle further includes a second connection portion 32. The first airflow guide portion 31 is connected to the inner wall of the airflow channel 11 through the second connection portion 32.

Figure 15:
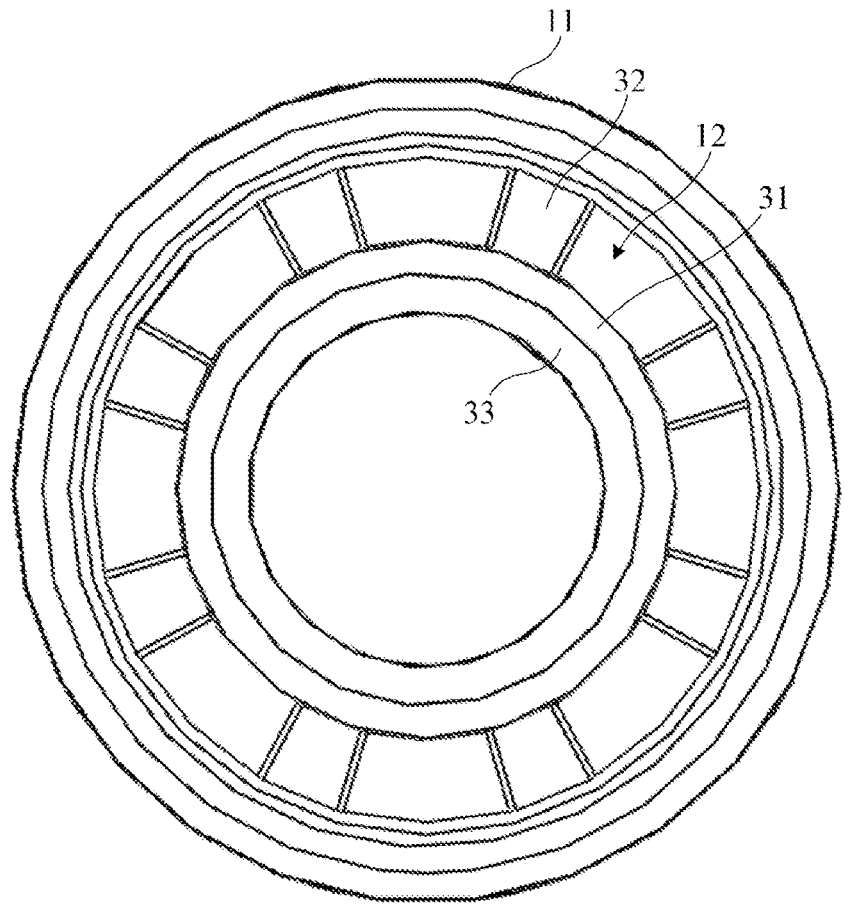
FIG. 15 is a schematic top structural diagram of a fourth embodiment of a vaporization suction nozzle according to this application.

Specifically, referring to FIG. 15 together, a plurality of second connection portions 32 are arranged between the first airflow guide portion 31 and the inner wall of the airflow channel 11. The plurality of second connection portions 32 are spaced in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channels 12 between the first airflow guide portion 31 and the inner wall of the airflow channel 11 is ensured.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 14, the airflow guide member further includes a second airflow guide portion 33. The second airflow guide portion 33 is arranged on one side of the first airflow guide portion 31 away from the air outlet 13, that is, the first airflow guide portion 31 is closer to the air outlet 13 relative to the second airflow guide portion 33. The second airflow guide portion 33 is obliquely arranged in a direction away from the inner wall of the airflow channel 11 and the air outlet 13 to form the second air inlet channels 15, and airflows (as shown by arrows Q2 in FIG. 14, similarly hereinafter) entering through the second air inlet channels 15 are used to guide the vapor to be outputted from the air outlet 13, thereby speeding up the discharge of the vapor.

Specifically, the airflow entering through the second air inlet channel 15 flow to the first air inlet 16 along the second airflow guide portion 33 to be mixed with vapor at the first air inlet 16, and then carries the vapor to pass through the first air inlet 16 and to be outputted from the air outlet 13.

Optionally, the second airflow guide portion 33 may be in an annular shape corresponding to an inner space of the vaporization suction nozzle, and surrounds in a circumferential direction of the vaporization suction nozzle.

It is to be noted that, in this exemplary embodiment, the airflow guide member is located at an end of the vaporization suction nozzle away from the air outlet 13, so that the airflow guide member is as close as possible to the vaporization core of the electronic vaporization device after the vaporization suction nozzle is assembled to the electronic vaporization device. In this way, the airflow guided by the airflow guide member can drive the output of the vapor near the vaporization core to the most, and the problem of vapor retention near the vaporization core can be alleviated to the most, thereby alleviating the problem of vapor condensation near the vaporization core to the most.

Certainly, in other embodiments in this application, the airflow guide member and the second air inlet 18 in communication with the airflow guide member can be arranged at other positions in the axial direction of the vaporization suction nozzle, and the problem of vapor retention near the vaporization core can also be alleviated, which is not limited herein.

Figure 16:
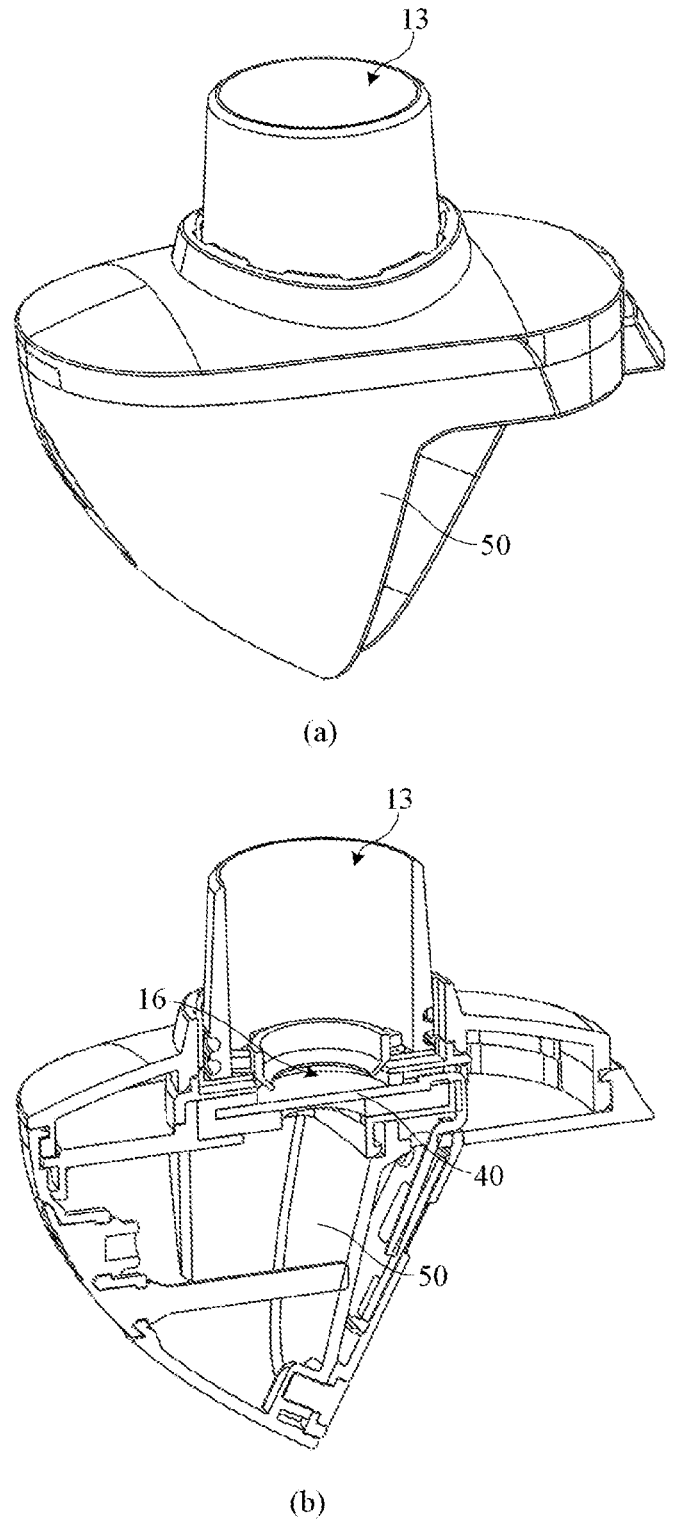
FIG. 16 is a schematic structural diagram of a second embodiment of a vaporizer according to this application.
Figure 17:
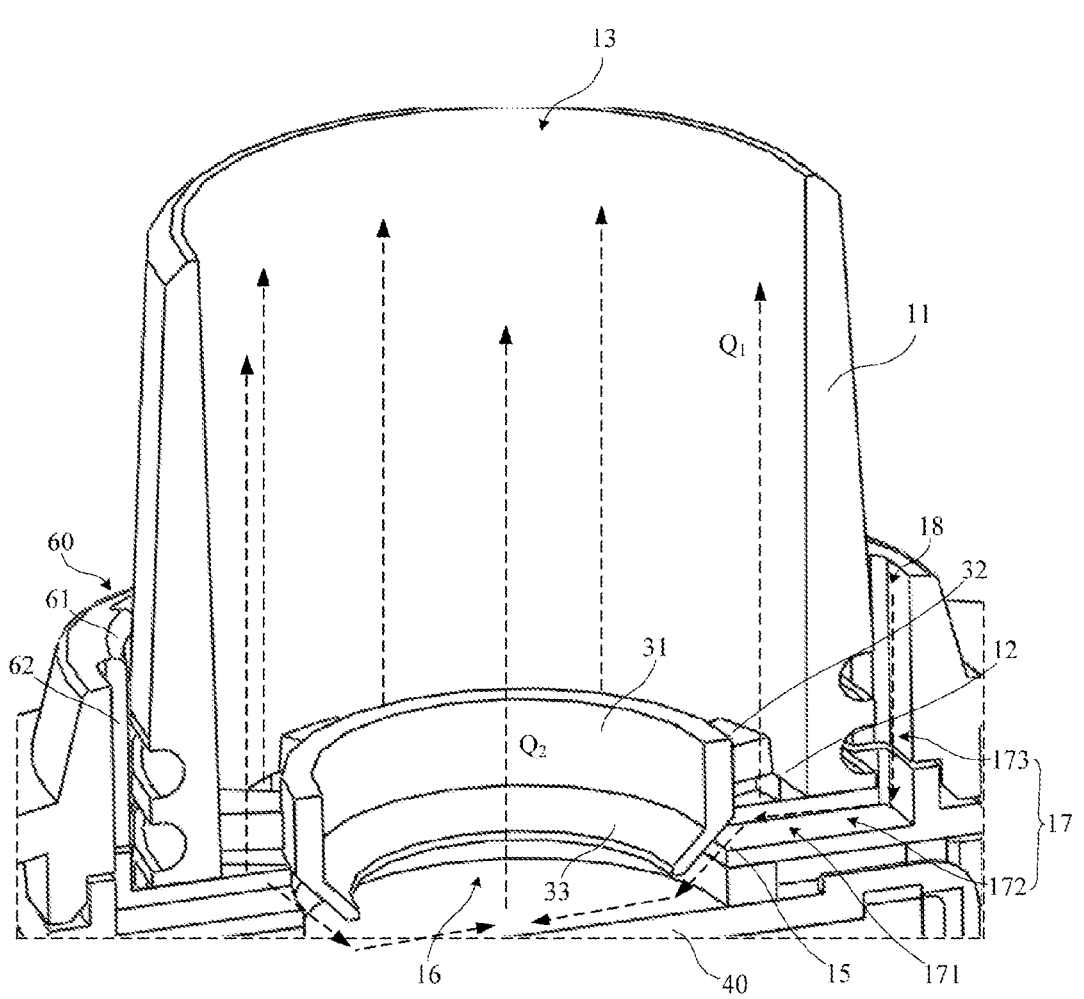
FIG. 17 is a schematic partial cross-sectional structural diagram of a second embodiment of a vaporizer according to this application.

Referring to FIG. 16 and FIG. 17, FIG. 16 is a schematic structural diagram of a second embodiment of a vaporizer according to this application, and FIG. 17 is a schematic partial cross-sectional structural diagram of a second embodiment of a vaporizer according to this application.

An exemplary embodiment in which the air-curtain forming structure is a vaporizer applicable to the electronic vaporization device is described below.

In this embodiment, the air-curtain forming structure is in a form of the vaporizer. The vaporizer provided in this embodiment is applicable to electronic vaporization devices such as an e-cigarette and a medical vaporizer. FIG. 16 shows a case in which the air-curtain forming structure is applicable to the medical vaporizer, which is merely used for description and is not intended to limit an application environment of the air-curtain forming structure in this embodiment.

In this embodiment, referring to FIG. 16, the air-curtain forming structure includes a vaporization suction nozzle, a vaporization core 40, and a liquid storage cavity 50. The vaporization suction nozzle includes a first air inlet 16 and an air outlet 13, vapor flows into the vaporization suction nozzle through the first air inlet 16 and is delivered to the air outlet 13 through the vaporization suction nozzle, and then the vapor is outputted from the air outlet 13 for the user to inhale. The vaporization core 40 is arranged at a position where the first air inlet 16 of the vaporization suction nozzle is located and is configured to vaporize an aerosol generation substrate stored in the liquid storage cavity 50 to generate vapor. The vapor generation device of the air-curtain forming structure in this embodiment includes structures such as the vaporization core 40 and the liquid storage cavity 50, and is configured to generate vapor.

For the case in which the air-curtain forming structure in this embodiment is applicable to the medical vaporizer, the vaporization core 40 may be an ultrasonic vaporization sheet, and the ultrasonic vaporization sheet vaporizes the aerosol generation substrate through high-frequency oscillation. The specific principle thereof falls within the understanding scope of a person skilled in the art, and details are not described herein again. Certainly, for the case in which the air-curtain forming structure is applied to other fields, the vaporization core 40 may also generate vapor in a manner of heating and vaporizing the aerosol generation substrate, which is not limited herein.

Specifically, referring to FIG. 17, the vaporization suction nozzle includes an airflow channel 11. The airflow channel 11 is configured to deliver vapor. The vaporization suction nozzle further includes first air inlet channels 12 in communication with the airflow channel 11, and the first air inlet channels 12 are configured to introduce external airflows into the airflow channel 11, so that blocking airflows (as shown by arrows Q1 in FIG. 11, similarly hereinafter) are formed between the inner wall of the airflow channel 17 and the vapor. The blocking airflows form an air curtain.

Further, the first air inlet 16 and the air outlet 13 are provided opposite to each other and are respectively in communication with the airflow channel 11. The first air inlet channels 12 are close to the inner wall of the airflow channel 11, and exits of the first air inlet channels 12 face the air outlet 13, to ensure that the airflows flowing into the airflow channel 11 through the first air inlet channels 12 can flow along the inner wall of the airflow channel 11 (that is, an inner wall of the vaporization suction nozzle), that is, the blocking airflows are formed to block the vapor and the inner wall of the airflow channel 11, that is, block the vapor and the inner wall of the vaporization suction nozzle, so that the vapor may be in contact with the inner wall of the vaporization suction nozzle as little as possible, thereby alleviating the problem of vapor condensation and reducing condensate generation.

Further, a flow direction of the blocking airflows is parallel to the inner wall of the airflow channel 11, that is, the flow direction of the blocking airflows is parallel to the inner wall of the vaporization suction nozzle, to ensure a desirable effect of the blocking airflows for blocking the vapor and the inner wall of the vaporization suction nozzle.

In an embodiment, still referring to FIG. 17, the vaporization suction nozzle further includes the second air inlet 18 different from the first air inlet 16, where the second air inlet 18 is configured to guide an external airflow to flow into the vaporization suction nozzle. The vaporization suction nozzle further includes an airflow guide member. The airflow guide member is in communication with the second air inlet 18 and is configured to guide the airflow entering through the second air inlet 18 to flow toward the first air inlet 16, and then carry vapor flowing into the vaporization suction nozzle through the first air inlet 16 and output the vapor through the air outlet 13 of the vaporization suction nozzle, so that the user can inhale and the discharge of the vapor can be accelerated.

In other words, the airflow guide member is configured to guide the airflow to flow toward the vaporization core 40, to drive the vapor near the vaporization core 40 to be outputted from the air outlet 13, so that the problem of vapor retention near the vaporization core 40 can be effectively alleviated, thereby alleviating the problem of vapor condensation near the vaporization core 40.

Specifically, at least a part of the airflow guide member is obliquely arranged in a direction away from the inner wall and the air outlet 13 of the vaporization suction nozzle, to guide the airflow entering through the second air inlet 18 to flow toward the first air inlet 16, that is, guide the airflow to flow toward the vaporization core 40 to directly face a surface of the vaporization core 40, to carry vapor vaporized by the vaporization core 40 to flow into the vaporization suction nozzle through the first air inlet 16 and to be outputted from the air outlet 13, and speed up the discharge of the vapor, so that less vapor is in contact with the inner wall of the vaporization suction nozzle to some extent, thereby alleviating the problem vapor condensation, and reducing condensate generation.

In an embodiment, still referring to FIG. 17, the airflow guide member includes a first airflow guide portion 31. The first air inlet channels 12 are formed between the first airflow guide portion 31 and the inner wall of the airflow channel 11 (that is, the inner wall of the vaporization suction nozzle), and are configured to guide airflows entering through the first air inlet channels 12 to flow along the inner wall of the airflow channel 11, where the airflow s entering through the first air inlet channels 12 are used to form blocking airflows between the inner wall of the vaporization suction nozzle and the vapor.

Further, the vaporization suction nozzle further includes a second connection portion 32. The first airflow guide portion 31 is connected to the inner wall of the airflow channel 11 through the second connection portion 32.

Specifically, a plurality of second connection portions 32 are arranged between the first airflow guide portion 31 and the inner wall of the airflow channel 11. The plurality of second connection portions 32 are spaced in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channels 12 between the first airflow guide portion 31 and the inner wall of the airflow channel 11 is ensured.

Optionally, the first airflow guide portion 31 may be in an annular shape corresponding to an inner space of the vaporization suction nozzle, and surrounds in a circumferential direction of the vaporization suction nozzle. In an embodiment, still referring to FIG. 17, the airflow guide member further includes a second airflow guide portion 33. The second airflow guide portion 33 is arranged on one side of the first airflow guide portion 31 away from the air outlet 13, that is, the first airflow guide portion 31 is closer to the air outlet 13 relative to the second airflow guide portion 33. The second airflow guide portion 33 is obliquely arranged in a direction away from the inner wall of the airflow channel 11 and the air outlet 13 to form the second air inlet channels 15, and airflows entering through the second air inlet channels 15 are used to guide the vapor to be outputted from the air outlet 13, thereby speeding up the discharge of the vapor.

Specifically, the airflow entering through the second air inlet channel 15 flow to the first air inlet 16 along the second airflow guide portion 33 to be mixed with vapor at the first air inlet 16, and then carries the vapor to pass through the first air inlet 16 and to be outputted from the air outlet 13.

Optionally, the second airflow guide portion 33 may be in an annular shape corresponding to an inner space of the vaporization suction nozzle, and surrounds in a circumferential direction of the vaporization suction nozzle.

In an embodiment, still referring to FIG. 17, the air-curtain forming structure further includes a converging channel 17, one end of the converging channel 17 is an air inlet, that is, a second air inlet 18, and the other end of the converging channel 17 is a diverging opening 171, where the diverging opening 171 is respectively in communication with the first air inlet channels 12 and the second air inlet channels 15.

Specifically, the converging channel 17 includes a first channel section 172 and a second channel section 173 that are in communication with each other, an end opening of the first channel section 172 away from the second channel section 173 is the diverging opening 171, and an end opening of the second channel section 173 away from the first channel section 172 is the air inlet, that is, the second air inlet 18. An extending direction of the first channel section 172 is different from an extending direction of the second channel section 173.

FIG. 17 shows that the extending direction of the first channel section 172 is a horizontal direction, the extending direction of the second channel section 173 is a vertical direction, and the second channel section 173 extends toward the air outlet 13. When the user inhales, an external airflow flows into the second channel section 173 through the second air inlet 18 and is delivered into the first channel section 172, and then the airflow passes through the diverging opening 171 and flows into the airflow channel 11 in the vaporization suction nozzle respectively through the first air inlet channels 12 and the second air inlet channels 15, where flow conditions of airflows are shown by dashed arrows in FIG. 17.

Further, the air-curtain forming structure includes a mounting portion 60. The mounting portion 60 includes a mounting protrusion 61 and a vent groove 62, where the mounting protrusion 61 is configured to fix the vaporization suction nozzle. After the vaporization suction nozzle is fixed to the mounting portion 60, the first channel section 172 is formed between the vaporization suction nozzle and the mounting portion 60, and to be specific, the first channel section 172 is formed between the vaporization suction nozzle and the bottom of the mounting portion 60. In addition, the second channel section 173 is formed between the vent groove 62 and the vaporization suction nozzle.

Figure 18:
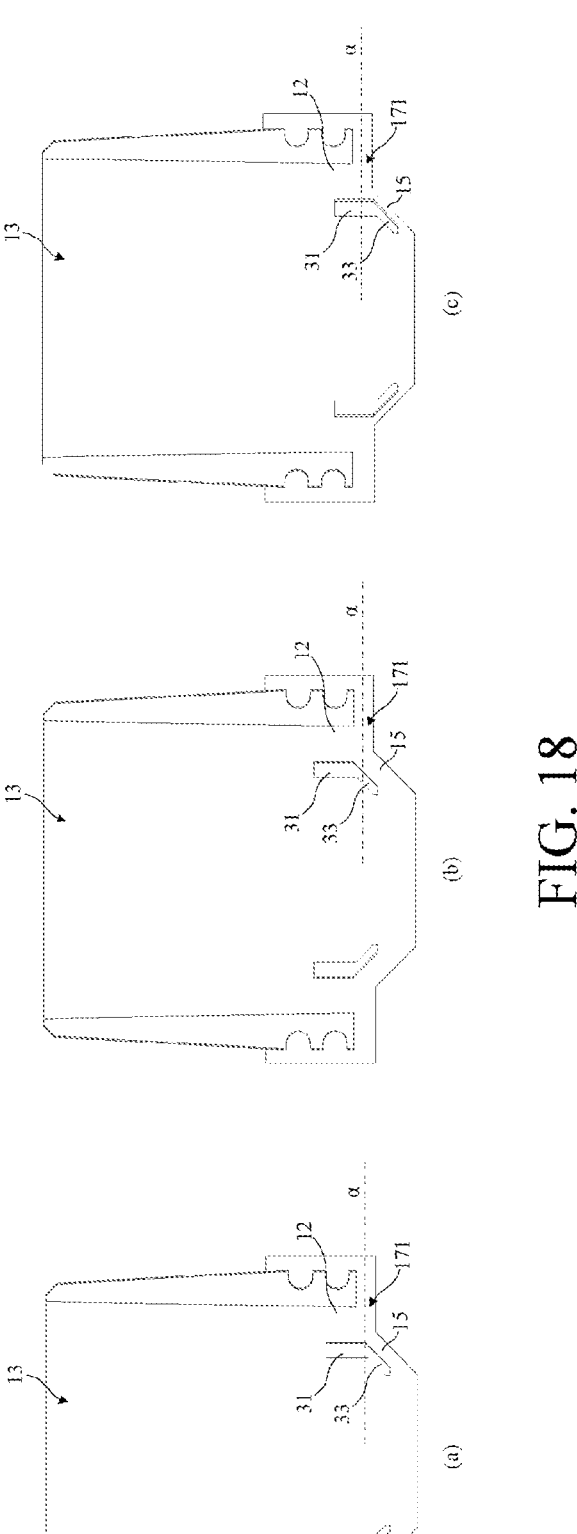
FIG. 18 is a schematic structural diagram of a relative position relationship between a center line of a diverging opening and a joint of a first airflow guide portion and a second airflow guide portion of a vaporizer according to this application.

Referring to FIG. 18, FIG. 18 is a schematic structural diagram of a relative position relationship between a center line of a diverging opening and a joint of a first airflow guide portion and a second airflow guide portion of a vaporizer according to this application. Airflow conditions in the first air inlet channel 12 and the second air inlet channel 15 in this exemplary embodiment are described below.

In this exemplary embodiment, the airflow entering through the first air inlet channel 12 forms the blocking airflow between the inner wall of the vaporization suction nozzle and the vapor, so that the vapor is in contact with the inner wall of the vaporization suction nozzle as little as possible, thereby alleviating the problem of vapor condensation, and reducing condensate generation. In addition, the airflow entering through the second air inlet channel 15 guides the vapor to be outputted from the air outlet 13, to speed up the discharge of the vapor, thereby effectively alleviating the problem of vapor condensation in a cavity surrounded by the airflow guide member.

Since the air pressure difference caused by user inhaling is fixed, a total amount of the airflows flowing into the first air inlet channel 12 and the second air inlet channel 15 is fixed. Therefore, in this exemplary embodiment, the amount of the airflows flowing into the first air inlet channel 12 and the second air inlet channel 15 is appropriately allocated, to alleviate the problem of vapor condensation on the inner wall of the vaporization suction nozzle and in the cavity surrounded by the airflow guide member.

In an embodiment, a center line a of the diverging opening 171 (where the center line a of the diverging opening 171 is defined as being perpendicular to a central axis of the diverging opening 171, similarly hereinafter) extends through the joint of the first airflow guide portion 31 and the second airflow guide portion 33, as shown in FIG. 18a. In this way, the airflow entering through the first air inlet channel 12 is sufficient to form the blocking airflow between the inner wall of the vaporization suction nozzle and the vapor, so that the adhesion degree of the vapor on the inner wall of the vaporization suction nozzle is reduced. In addition, the airflow entering through the second air inlet channel 15 is sufficient to quickly carry and discharge the vapor, so that the adhesion degree of the vapor in the cavity surrounded by the airflow guide member is reduced.

In an alternative embodiment, the center line a of the diverging opening 171 is away from the air outlet 13 relative to the joint of the first airflow guide portion 31 and the second airflow guide portion 33, as shown in FIG. 18b. In this way, the amount of the airflow entering through the second air inlet channel 15 is significantly increased, which can further speed up carrying and discharging the vapor, further reduce the adhesion degree of the vapor in the cavity surrounded by the airflow guide member, thereby alleviating the problem of vapor condensation in the cavity surrounded by the airflow guide member.

In another alternative embodiment, the center line a of the diverging opening 171 is close to the air outlet 13 relative to the joint of the first airflow guide portion 31 and the second airflow guide portion 33, as shown in FIG. 18c. In this way, the amount of the airflow entering through the first air inlet channel 12 is significantly increased, which can further increase an amount of the blocking airflows between the inner wall of the vaporization suction nozzle and the vapor, and further reduce the adhesion degree of the vapor on the inner wall of the vaporization suction nozzle, thereby alleviating the problem of vapor condensation on the inner wall of the vaporization suction nozzle.

It is to be noted that, a size relationship between the cross-sectional area of the first air inlet channel 12 and that of the second air inlet channel 15 is the same as an airflow amount relationship between the airflow of the first air inlet channel 12 and that of the second air inlet channel 15. That is to say, the cross-sectional area of the first air inlet channel 12 being greater than the cross-sectional area of the second air inlet channel 15 indicates that the airflow amount of the first air inlet channel 12 being greater than the airflow amount of the second air inlet channel 15, or otherwise, the opposite.

In view of this, in this exemplary embodiment, the cross-sectional area of the second air inlet channel 15 can be adjusted by adjusting a degree of inclination of the second airflow guide portion 33 of the airflow guide member, so that the size relationship between the cross-sectional area of the first air inlet channel 12 and that of the second air inlet channel 15 can be adjusted, thereby adjusting the airflow amount of the first air inlet channel 12 and the second air inlet channel 15.

Specifically, the second airflow guide portion 33 being more inclined in a direction away from the air outlet 13 indicates a smaller cross-sectional area of the second air inlet channel 15, which indicates a smaller airflow amount of the second air inlet channel 15 and a larger airflow amount of the first air inlet channel 12, or otherwise, the opposite.

It is to be noted that, in the foregoing manner, the adhesion degrees of the vapor on the inner wall of the vaporization suction nozzle and the vapor in the cavity surrounded by the airflow guide member are less than 3%. It can be seen that, based on the design of the first air inlet channel 12 and the second air inlet channel 15 in this exemplary embodiment, the adhesion degree of the vapor can be effectively reduced, thereby alleviating the problem of vapor condensation.

Figure 19:
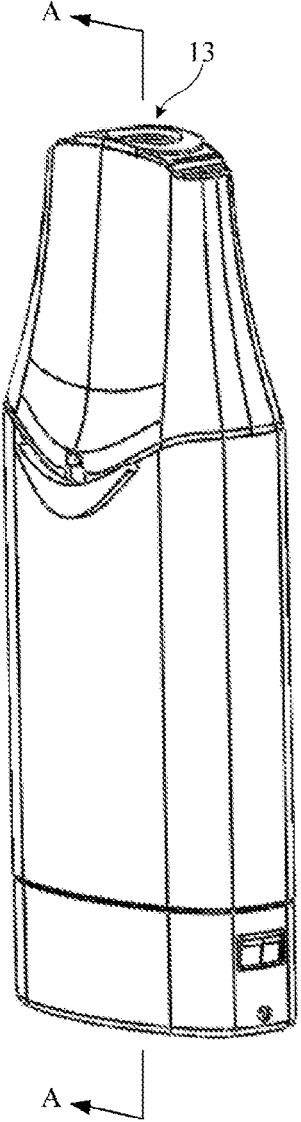
FIG. 19 is a schematic structural diagram of a third embodiment of a vaporizer according to this application.
Figure 20:
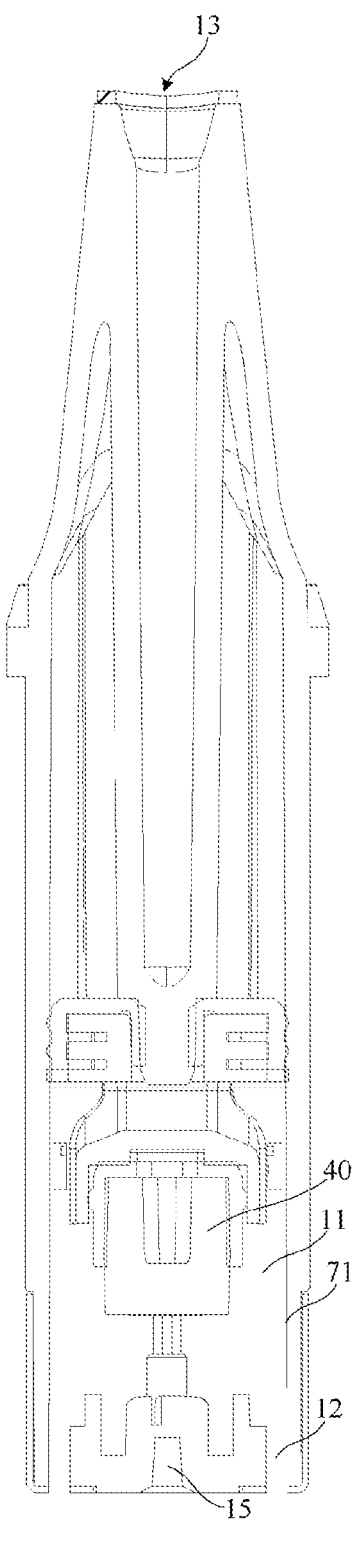
FIG. 20 is a schematic cross-sectional structural diagram of a third embodiment of a vaporizer in a direction A-A according to this application.

Referring to FIG. 19 and FIG. 20, FIG. 19 is a schematic structural diagram of a third embodiment of a vaporizer according to this application, and FIG. 20 is a schematic cross-sectional structural diagram of a third embodiment of a vaporizer in a direction A-A according to this application.

An exemplary embodiment in which the air-curtain forming structure is a vaporizer applicable to the electronic vaporization device is described below.

In this embodiment, the air-curtain forming structure is in a form of the vaporizer. The vaporizer provided in this embodiment is applicable to electronic vaporization devices such as an e-cigarette and a medical vaporizer. FIG. 19 shows a case in which the air-curtain forming structure is applicable to the e-cigarette, which is merely used for description and is not intended to limit an application environment of the air-curtain forming structure in this embodiment.

Specifically, the vaporizer includes an airflow channel 11. The airflow channel 11 is configured to deliver vapor. The vaporizer further includes a first air inlet channel 12 in communication with the airflow channel 11, and the first air inlet channel 12 is configured to introduce an external airflow into the airflow channel 11, so that a blocking airflow is formed between an inner wall of the airflow channel 11 and the vapor. The blocking airflows form an air curtain.

Further, the vaporizer further includes an air outlet 13 in communication with the airflow channel 11, the first air inlet channel 12 is close to the inner wall of the airflow channel 11, and an exit of the first air inlet channel 12 faces the air outlet 13, to ensure that the airflow flowing into the airflow channel 11 through the first air inlet channel 12 can flow along the inner wall of the airflow channel 11 (that is, an inner wall of the vaporizer), that is, the blocking airflow are formed to block the vapor and the inner wall of the airflow channel 11, that is, block the vapor and the inner wall of the vaporizer, so that the vapor may be in contact with the inner wall of the vaporizer as little as possible, thereby alleviating the problem of vapor condensation and reducing condensate generation.

In an embodiment, still referring to FIG. 20, the vaporizer further includes a vaporization cavity 71. A vaporization core 40 is arranged in the vaporization cavity 71 and is configured to vaporize an aerosol generation substrate to generate vapor. The airflow channel 11 is provided in the vaporization cavity 71, that is, a space used for accommodating the vaporization cavity 71 is the airflow channel 11. A first air inlet channel 12 is provided on the bottom of the vaporization cavity 71 close to an inner wall of the vaporization cavity 71, so that an airflow flowing into the vaporization cavity 71 through the first air inlet channel 12 during user inhaling may flow along the inner wall of the vaporization cavity 71, thereby forming a blocking airflow between the inner wall of the vaporization cavity 71 and the vapor.

Further, the vaporizer further includes a second air inlet channel 15, an airflow entering through the second air inlet channel 15 is used to guide the vapor to be outputted from the air outlet 13, to speed up the discharge of the vapor, so that less vapor is in contact with the inner wall of the vaporization cavity 71 to some extent, and the problem of vapor condensation can also be alleviated. Specifically, the second air inlet channel 15 is provided on the bottom of the vaporization cavity 71, and the first air inlet channel 12 is close to an edge of the bottom of the vaporization cavity 71 relative to the second air inlet channel 15.

Figure 21:
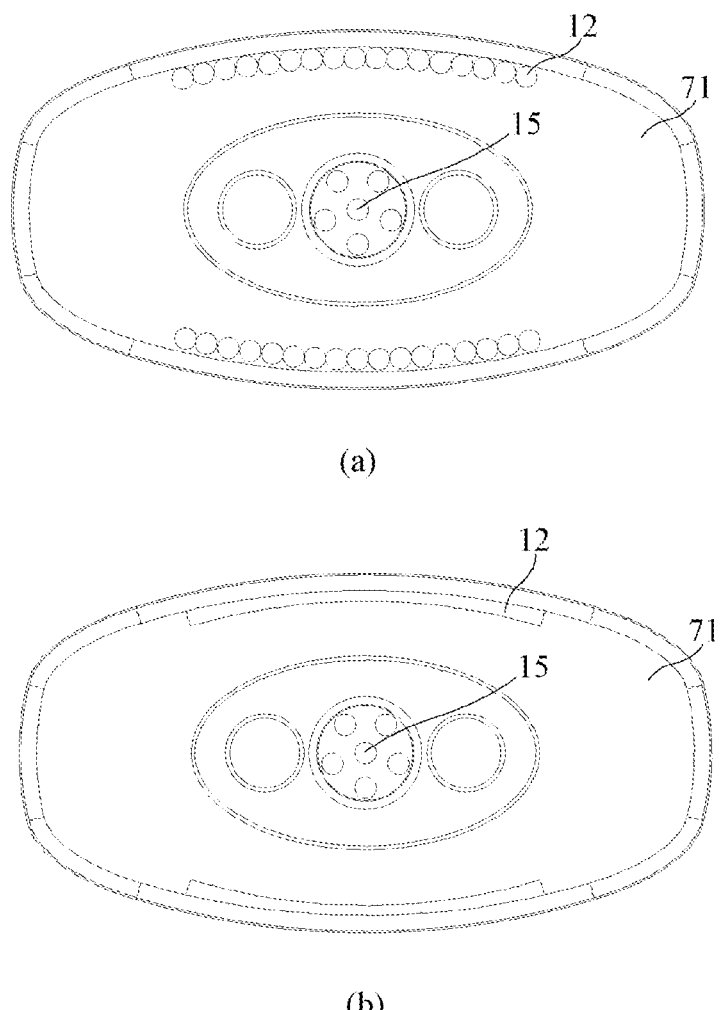
FIG. 21 is a schematic bottom structural diagram of a third embodiment of a vaporizer according to this application.

Furthermore, referring to FIG. 21, the first air inlet channels 12 are respectively provided on two opposite sides of the second air inlet channels 15. Based on the foregoing manner, a quantity of the first air inlet channels 12 can be increased, to further reduce contact between the vapor and the inner wall of the vaporization cavity 71, thereby further alleviating the problem of vapor condensation. In addition, the first air inlet channels 12 are provided on opposite sides of the second air inlet channels 15 as symmetrically as possible, so that the distribution of the blocking airflows in the vaporization cavity 71 can be optimized, thereby improving the effect of alleviating the problem of vapor condensation.

In an embodiment, the first air inlet channels 12 may be in a through-hole form, as shown in FIG. 21a. A plurality of first air inlet channels 12 are spaced on the bottom of the vaporization cavity 71 close to the inner wall of the vapor-ization cavity 71, and airflows flowing into the vaporization cavity 71 through the first air inlet channels 12 in the through-hole form may form blocking airflows. Specifically, the plurality of first air inlet channels 12 are spaced along an edge on the bottom of the vaporization cavity 71, and the plurality of first air inlet channels 12 are spaced on two opposite sides of the second air inlet channels 15.

Optionally, the hole diameter of the first air inlet channel 12 in the through-hole form may be 0.3 mm, 0.4 mm, or the like, which is not limited herein.

In an alternative embodiment, a cross section of the first air inlet channel 12 is strip-shaped, that is, the first air inlet channel 12 is a strip-shaped narrow gap, as shown in FIG. 21b. The first air inlet channels 12 in the narrow-gap form extend along the edge on the bottom of the vaporization cavity 71, and airflows flowing into the vaporization cavity 71 through the first air inlet channels 12 in the narrow-gap form may form the blocking airflows. Further, the first air inlet channels 12 in the narrow-gap form are respectively provided on two opposite sides of the second air inlet channels 15.

Optionally, the width of the first air inlet channel 12 in the narrow-gap form may be 0.3 mm, 0.4 mm, or the like, which is not limited herein.

It is to be noted that, the distribution of the blocking airflows formed by the airflows entering through the first air inlet channel 12 in the narrow-gap form is better than the distribution of the blocking airflows formed by the airflows entering through the first air inlet channel 12 in the through-hole form, and the distribution of the blocking airflows formed by the airflows entering through the first air inlet channel 12 of a width of 0.4 mm is better than the distri-bution of the blocking airflows formed by the airflows entering through the first air inlet channel 12 of a width of 0.3 mm. In addition, an entire flow direction of airflows inside the vaporization cavity 71 is more ordered because of the function of the blocking airflows, so that a vortex flow is unlikely to be formed.

Figure 22:
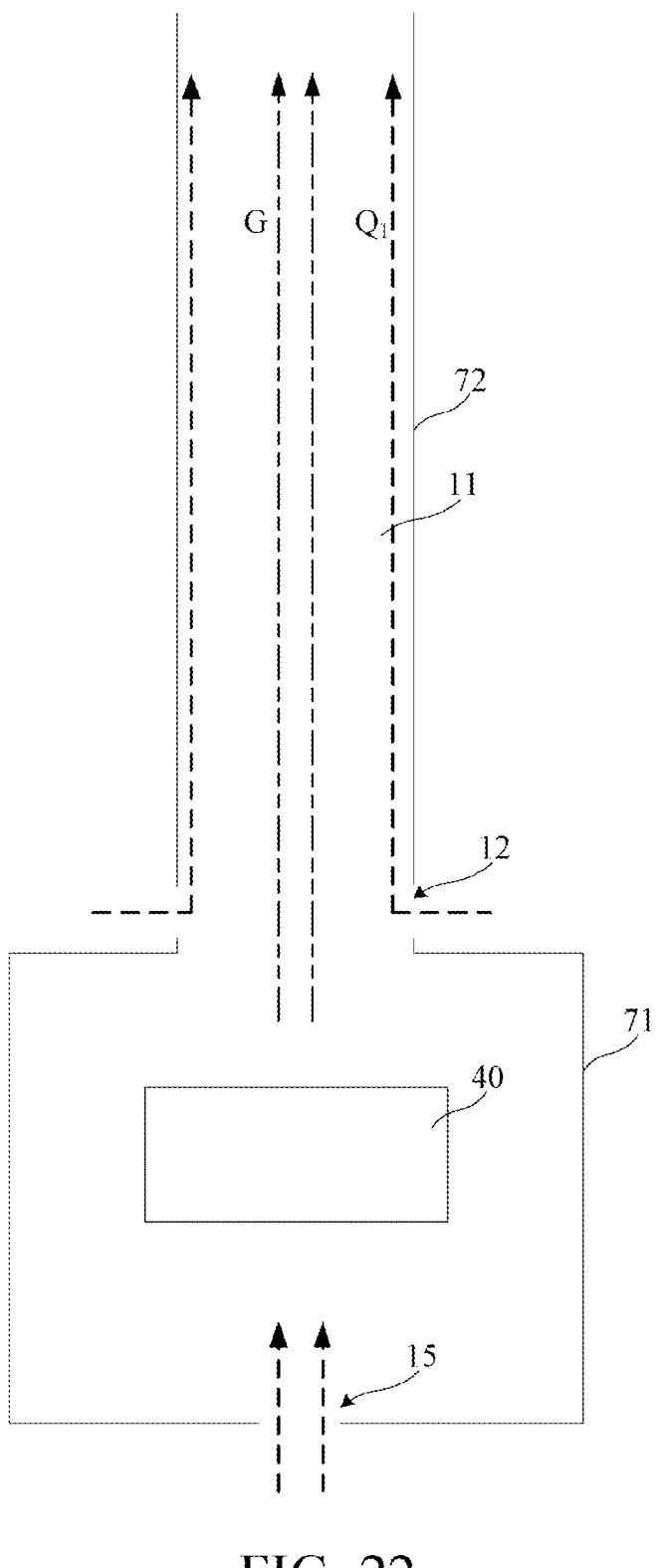
FIG. 22 is a schematic structural diagram of a fourth embodiment of a vaporizer according to this application.

Referring to FIG. 22, FIG. 22 is a schematic structural diagram of a fourth embodiment of a vaporizer according to this application.

An exemplary embodiment in which the air-curtain form-ing structure is a vaporizer applicable to the electronic vaporization device is described below.

In this embodiment, the air-curtain forming structure is in a form of the vaporizer. The vaporizer provided in this embodiment is applicable to electronic vaporization devices such as an e-cigarette and a medical vaporizer. FIG. 22 shows a case in which the air-curtain forming structure is applicable to the e-cigarette, which is merely used for description and is not intended to limit an application environment of the air-curtain forming structure in this embodiment.

Specifically, the vaporizer includes an airflow channel 11. The airflow channel 11 is configured to deliver vapor. The vaporizer further includes a first air inlet channel 12 in communication with the airflow channel 11, and the first air inlet channel 12 is configured to introduce an external airflow into the airflow channel 11, so that a blocking airflow is formed between an inner wall of the airflow channel 11 and the vapor. The blocking airflows form an air curtain.

The vaporizer further includes an air outlet channel 72, the airflow channel 11 is provided in the air outlet channel 72, and the first air inlet channels 12 are provided on a side wall of the air outlet channel 72. When the user inhales, external airflows flow into the air outlet channel 72 through the first air inlet channels 12 on the side wall of the air outlet channel 72 and then flow along an inner wall of the air outlet channel 72, to form blocking airflows between the inner wall of the air outlet channel 72 and the vapor, thereby effectively reducing contact between high-temperature vapor in the air outlet channel 72 and the inner wall of the low-temperature air outlet channel 72, and reducing vapor condensation. As shown in FIG. 22, blocking airflows Q1 are located between the inner wall of the air outlet channel 72 and vapor G, to block the inner wall of the air outlet channel 72 and the vapor G.

Further, the vaporizer further includes a vaporization cavity 71. A vaporization core 40 is arranged in the vapor-ization cavity 71 and is configured to vaporize an aerosol generation substrate to generate vapor. The vaporization cavity 71 is in communication with the air outlet channel 72. In addition, a second air inlet channel 15 is provided in the vaporization cavity 71. When the user inhales, external airflows flow into the vaporization cavity 71 through the second air inlet channels 15, to carry the vapor in the vaporization cavity 71 to be discharged through the air outlet channel 72, which can speed up the discharge of the vapor, so that contact between the vapor and the inner wall of the vaporization cavity 71, and contact between the vapor and the inner wall of the air outlet channel 72 can be reduced to some extent, and the problem of vapor condensation can also be alleviated.

The first air inlet channels 12 are provided on a part of the air outlet channel 72 close to the vaporization cavity 71, as shown in FIG. 22, so that the vapor condensation of the air outlet channel 72 located between the first air inlet channels 12 and the vaporization cavity 71 can be avoided as much as possible, thereby further alleviating the problem of vapor condensation.

Figure 23:
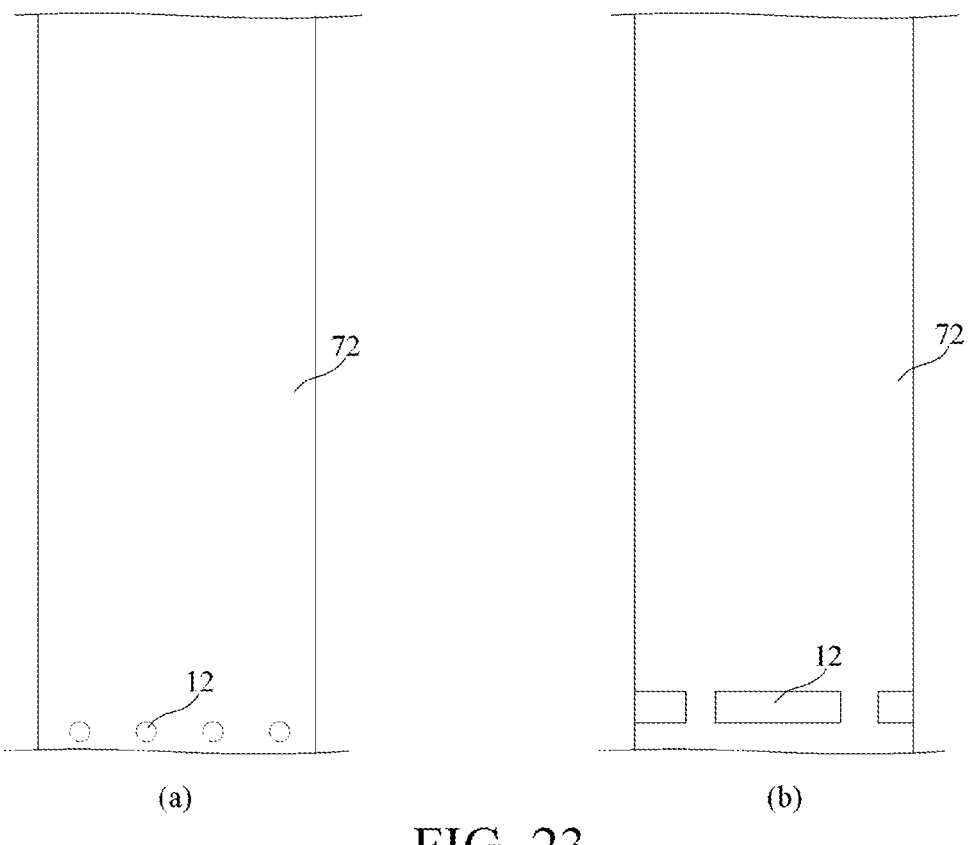
FIG. 23 is a schematic structural diagram of an embodiment of an air outlet channel according to this application.

Further, referring to FIG. 23, the vaporizer includes a plurality of first air inlet channels 12, where the plurality of first air inlet channels 12 are sequentially spaced apart from each other in a circumferential direction of the air outlet channel 72. Furthermore, the plurality of first air inlet channels 12 are evenly spaced in the circumferential direc-tion of the air outlet channel 72, so that airflows evenly flow into the side wall of the air outlet channel 72, thereby forming blocking airflows in the air-curtain form that are well distributed in the air outlet channel 72.

Optionally, the first air inlet channels 12 are preferably circular holes as shown in FIG. 23a or elongated holes as shown in FIG. 23b. In addition, the diameter of the first air inlet channel 12 in the circular-hole form may be 0.3 mm, 0.4 mm, or the like, and the width of the first air inlet channel 12 in the strip-shaped form may be 0.3 mm, 0.4 mm, or the like, which are not limited herein.

Referring to table in the following, the table shows an accumulation amount of condensate in a conventional air outlet channel and the air outlet channel 72 in this exemplary embodiment when the user inhales for different times.

| | Accumulation amount of condensate/mg | | |
| --- | --- | --- | --- |
| | 10/times | 30/times | 50/times |
| Conventional air outlet channel | 1.1 | 2.2 | 4.8 |
| Air outlet channel in this exemplary embodiment | 0.8 | 1.9 | 4.7 |

Based on the above, an air-curtain forming structure applicable to an electronic vaporization device is provided in this application, and the air-curtain forming structure includes an airflow channel configured to deliver vapor. The airflow channel includes a first air inlet channel, and the first air inlet channel is configured to introduce an external airflow into the airflow channel, so that a blocking airflow is formed between an inner wall of the airflow channel and the vapor. In this application, the blocking airflow is used to block the inner wall of the airflow channel and the vapor, so that the vapor is in contact with the inner wall of the airflow channel as little as possible, the problem of vapor condensation can be alleviated, and less condensate is generated, thereby improving the user experience, reducing drug loss, and reducing the risk of condensate leakage.

Figure 24:
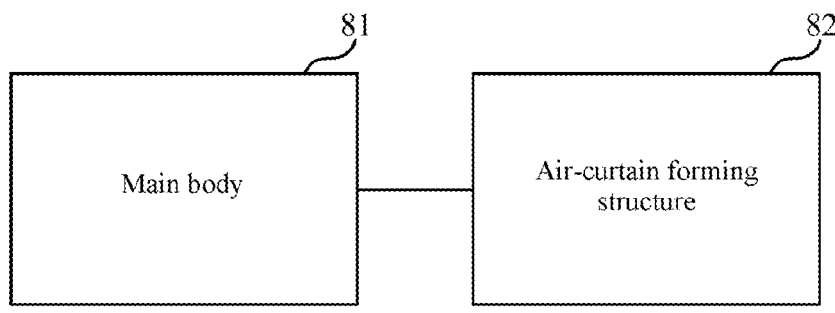
FIG. 24 is a schematic structural diagram of an embodiment of an electronic vaporization device according to this application.

Referring to FIG. 24, FIG. 24 is a schematic structural diagram of an embodiment of an electronic vaporization device according to this application.

In this embodiment, the electronic vaporization device may be an e-cigarette or a medical vaporization electronic device, and includes a main body 81 and an air-curtain forming structure 82, where the main body 81 is connected to the air-curtain forming structure 82, and the air-curtain forming structure 82 includes an airflow channel configured to deliver vapor. The air-curtain forming structure 82 further includes a first air inlet channel in communication with the airflow channel, and the first air inlet channel is configured to introduce an external airflow into the airflow channel, so that a blocking airflow is formed between an inner wall of the airflow channel and the vapor.

The air-curtain forming structure 82 is described in detail in the foregoing embodiments, and details are not described herein again.

It is to be noted that, the main body 81 is defined as a set of other elements of the electronic vaporization device other than the air-curtain forming structure 82. Specifically, when the air-curtain forming structure 82 is a vaporization suction nozzle applicable to the electronic vaporization device, the main body 81 includes a main unit (including a power supply and circuit parts of the electronic vaporization device) of the electronic vaporization device and other elements (including a vaporization core, and the like) of the vaporizer other than the vaporization suction nozzle. In addition, when the air-curtain forming structure 82 is the vaporizer applicable to the electronic vaporization device, the main body 81 includes the main unit of the electronic vaporization device.

Figure 25:
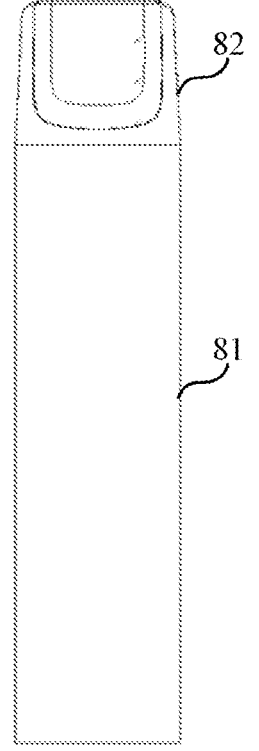
FIG. 25 is a schematic structural diagram of another embodiment of an electronic vaporization device according to this application.

For example, FIG. 25 shows an entire form of the device, that is, the electronic vaporization device, on which the main body 81 and the air-curtain forming structure 82 are assembled.

Figure 26:
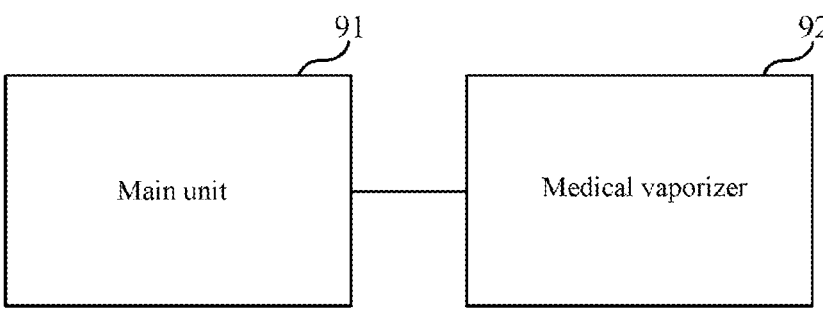
FIG. 26 is a schematic structural diagram of an embodiment of a medical vaporization electronic device according to this application.

Referring to FIG. 26, FIG. 26 is a schematic structural diagram of an embodiment of a medical vaporization electronic device according to this application.

In this embodiment, the medical vaporization electronic device is applicable to the field of medical vaporization and includes a main unit 91 (including a power supply and circuit parts of the medical vaporization electronic device) and a medical vaporizer 92 connected to the main unit 91. The medical vaporizer 92 includes a vaporization suction nozzle, where the vaporization suction nozzle includes a first air inlet, a second air inlet, and an air outlet. The medical vaporizer 92 further includes a liquid storage cavity, where the liquid storage cavity is configured to store an aerosol generation substrate. The medical vaporizer 92 further includes a vaporization core, where the vaporization core is located in the first air inlet and is configured to vaporize the aerosol generation substrate to generate vapor. The medical vaporizer 92 further includes an airflow guide member, where the airflow guide member is arranged in the vaporization suction nozzle and is in communication with the second air inlet, and the airflow guide member is configured to guide an airflow entering through the second air inlet to flow toward the vaporization core, to carry the vapor to be outputted from the air outlet.

The medical vaporizer 92 is described in detail in the foregoing embodiments, and details are not described herein again.

Figure 27:
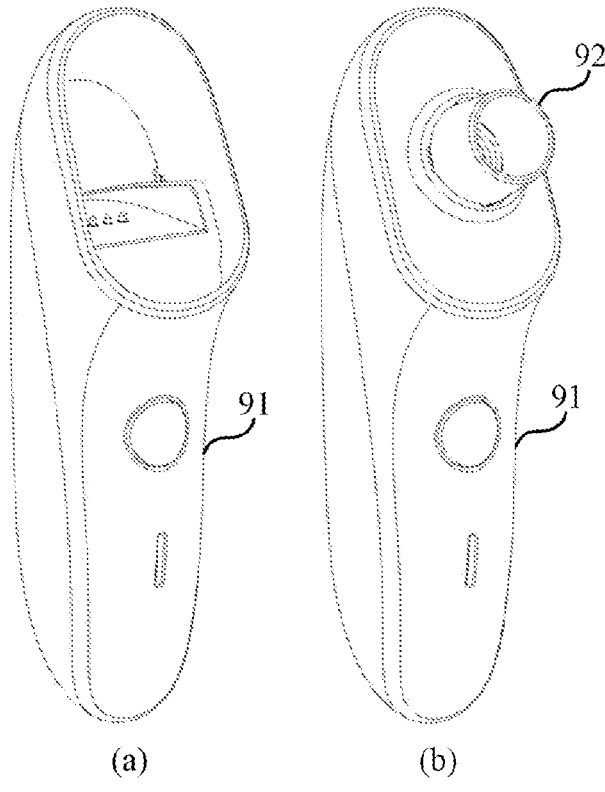
FIG. 27 is a schematic structural diagram of another embodiment of a medical vaporization electronic device according to this application.

For example, FIG. 27*a* shows an exemplary embodiment of the main unit 91, and FIG. 27*b* shows an entire form of the device, that is, the medical vaporization electronic device, on which the main unit 91 and the medical vaporizer 92 are assembled.

In this application, unless otherwise explicitly specified or defined, the terms such as "connect", "connection", and "stack" should be understood in a broad sense. For example, the connection may be a fixed connection, a detachable connection, or an integral connection; or the connection may be a direct connection, an indirect connection through an intermediate medium, internal communication between two elements, or an interaction relationship between two elements. A person of ordinary skill in the art may understand the specific meanings of the foregoing terms in this application according to specific situations.

Finally, it is to be noted that the foregoing embodiments are merely used for describing technical solutions of this application, but are not intended to limit this application. Although this application is described in detail with reference to the foregoing embodiments, a person of ordinary skill in the art is to understand that, modifications may still be made to the technical solutions in the foregoing embodiments, or equivalent replacements may be made to some or all of the technical features; and these modifications or replacements will not cause the essence of corresponding technical solutions to depart from the scope of the technical solutions in the embodiments of this application.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. An air-curtain forming structure applicable to an electronic vaporization device, comprising:

an airflow channel configured to deliver vapor, the airflow channel extending in an axial direction, the airflow channel having an inner wall, the inner wall extending parallel to the axial direction and circumferentially around the axial direction;

a first air inlet channel in communication with the airflow channel and configured to introduce an external airflow into the airflow channel so as to form a blocking airflow at a first radial distance relative to the vapor between the inner wall of the airflow channel and the vapor; and a second air inlet channel in communication with the airflow channel, the second air inlet channel being configured to introduce a second external airflow into the airflow channel so as to form a second airflow at a second radial distance relative to the vapor between the inner wall of the airflow channel and the vapor, wherein the first radial distance is greater than the second radial distance such that the blocking airflow is formed closer to the inner wall of the airflow channel than the second airflow.

2. The air-curtain forming structure according to claim 1, wherein a flow direction of the blocking airflow is parallel to the inner wall of the airflow channel.

3. The air-curtain forming structure of claim 1, further comprising:

an air outlet in communication with the airflow channel, an exit of the first air inlet channel facing the air outlet.

4. The air-curtain forming structure of claim 3, wherein the air-curtain forming structure comprises a vaporization suction nozzle applicable to the electronic vaporization device, and wherein the vaporization suction nozzle comprises an airway body and a tube body, the airflow channel is provided in the airway body and the tube body, an end of the tube body away from the airway body comprises the air outlet, and the first air inlet channel is provided at a position of the airway body close to an inner wall of the tube body such that the blocking airflow is formed between the inner wall of the tube body and the vapor.

5. The air-curtain forming structure of claim 4, wherein the airway body comprises a first airway portion, a second airway portion, and a wall portion, and the airflow channel further comprises an entrance channel and an air guide channel that are in communication with each other, wherein the entrance channel is provided in the first airway portion, the air guide channel is provided in the tube body, the second airway portion is sleeved on a periphery of the tube body, and the wall portion is connected to the first airway portion and the second airway portion and covers the air guide channel, and wherein the first air inlet channel is provided on the wall portion.

6. The air-curtain forming structure of claim 5, wherein the airflow channel comprises a plurality of first air inlet channels spaced apart from each other in a circumferential direction of the wall portion.

7. The air-curtain forming structure of claim 5, wherein the first airway portion further comprises a vent portion and a first connection portion, and the vent portion is connected to the wall portion through the first connection portion, and wherein a cross-sectional area of the first connection portion is less than a cross-sectional area of the vent portion such that a clamping opening is formed at a position where the first connection portion is located, and the clamping opening is configured to clamp a vapor generation device of the electronic vaporization device.

8. The air-curtain forming structure of claim 7, wherein a second air inlet channel is provided in the vent portion, and wherein an airflow entering through the second air inlet channel is used to guide the vapor to be outputted from the air outlet.

9. The air-curtain forming structure of claim 8, wherein the second air inlet channel comprises an air inlet portion and an air guide portion, the air inlet portion is configured to introduce the external airflow into the air guide portion, the air inlet portion is in communication with the airflow channel through the air guide portion, and an extending direction of the air guide portion is parallel to an extending direction of the entrance channel.

10. The air-curtain forming structure of claim 8, wherein a comprehensive airway is formed at a position where the clamping opening is located, and wherein the comprehensive airway is respectively in communication with the first air inlet channel and the second air inlet channel.

11. The air-curtain forming structure of claim 8, wherein the first air inlet channel is provided corresponding to the second air inlet channel, or wherein the first air inlet channel and the second air inlet channel are staggered.

12. The air-curtain forming structure of claim 8, wherein a cross-sectional area of the first air inlet channel is greater than a cross-sectional area of the second air inlet channel, and/or wherein a quantity of the first air inlet channels is greater than a quantity of the second air inlet channels.

13. The air-curtain forming structure of claim 3, further comprising:

a first airflow guide portion, wherein the first air inlet channel is formed between the first airflow guide portion and the inner wall of the airflow channel, and wherein the first airflow guide portion is configured to guide the airflow introduced through the first air inlet channel to flow along the inner wall of the airflow channel so as to form the blocking airflow.

14. The air-curtain forming structure of claim 13, further comprising:

a second connection portion, wherein the first airflow guide portion is connected to the inner wall of the airflow channel through the second connection portion.

15. The air-curtain forming structure of claim 14, wherein a plurality of second connection portions are arranged between the first airflow guide portion and the inner wall of the airflow channel, the plurality of second connection portions are sequentially spaced in a circumferential direction of the first airflow guide portion, and the first air inlet channel is formed between adjacent second connection portions.

16. The air-curtain forming structure of claim 13, further comprising:

a second airflow guide portion, wherein the second airflow guide portion is away from the inner wall of the airflow channel relative to the first airflow guide portion, and wherein the second air inlet channel is formed between the second airflow guide portion and the first airflow guide portion, an exit of the second air inlet channel faces the air outlet, and an airflow entering through the second air inlet channel is used to guide the vapor to be outputted from the air outlet.

17. The air-curtain forming structure of claim 16, wherein an angle between a flow direction of the airflow entering through the second air inlet channel and a preset direction ranges from 30° to 45°, and wherein the preset direction is parallel to a flow direction of the blocking airflow.

18. The air-curtain forming structure of claim 16, further comprising:

a third connection portion, wherein the second airflow guide portion is connected to the first airflow guide portion through the third connection portion.

19. The air-curtain forming structure of claim 18, wherein a plurality of third connection portions are arranged between the second airflow guide portion and the first airflow guide portion, the plurality of third connection portions are sequentially spaced in a circumferential direction of the second airflow guide portion, and the second air inlet channel is formed between adjacent third connection portions.

20. The air-curtain forming structure of claim 13, further comprising:

a second airflow guide portion arranged on one side of the first airflow guide portion away from the air outlet, wherein the second airflow guide portion is obliquely arranged in a direction away from the inner wall of the airflow channel and the air outlet to form the second air inlet channel, wherein an airflow entering through the second air inlet channel is used to guide the vapor to be outputted from the air outlet.

21. The air-curtain forming structure of claim 20, wherein the air-curtain forming structure comprises a vaporizer applicable to the electronic vaporization device, wherein the vaporizer comprises a vaporization suction nozzle and a vapor generation device, wherein the second airflow guide portion is arranged in the vaporization suction nozzle, and wherein the second air inlet channel is formed between the second airflow guide portion and the vapor generation device.

22. The air-curtain forming structure of claim 21, further comprising: a converging channel, wherein one end of the converging channel comprises an air inlet and an other end of the converging channel comprises a diverging opening, and wherein the diverging opening is respectively in communication with the first air inlet channel and the second air inlet channel.

23. The air-curtain forming structure of claim 22, wherein a center line of the diverging opening extends through a joint of the first airflow guide portion and the second airflow guide portion.

24. The air-curtain forming structure of claim 22, wherein a center line of the diverging opening passes between the first airflow guide portion and the second airflow guide portion.

25. The air-curtain forming structure of claim 22, wherein the converging channel comprises a first channel section and a second channel section that are in communication with each other, wherein an end opening of the first channel section away from the second channel section comprises the diverging opening, wherein an end opening of the second channel section away from the first channel section comprises the air inlet, and wherein an extending direction of the first channel section is different from that of the second channel section.

26. The air-curtain forming structure of claim 21, wherein the vapor generation device comprises a mounting portion, the mounting portion comprises a mounting protrusion and a vent groove, and the mounting protrusion is configured to fix the vaporization suction nozzle, wherein the first channel section is formed between the vaporization suction nozzle and the mounting portion, and wherein the second channel section is formed between the vent groove and the vaporization suction nozzle.

27. The air-curtain forming structure of claim 21, wherein a periphery of the vaporization suction nozzle is provided with limiting grooves surrounding in a circumferential direction thereof, and wherein the limiting grooves are configured to place elastic rings such that the vaporization suction nozzle is fixed to the vapor generation device.

28. The air-curtain forming structure of claim 3, wherein the air-curtain forming structure comprises a vaporizer applicable to the electronic vaporization device, wherein the vaporizer comprises a vaporization cavity, wherein the airflow channel is provided in the vaporization cavity, and wherein the first air inlet channel is provided at a position on the bottom of the vaporization cavity close to an inner wall of the vaporization cavity such that the blocking airflow is formed between the inner wall of the vaporization cavity and the vapor.

29. The air-curtain forming structure of claim 28, wherein the vaporizer further comprises a second air inlet channel, wherein an airflow entering through the second air inlet channel is used to guide the vapor to be outputted from the air outlet, wherein the second air inlet channel is provided on a bottom of the vaporization cavity, and wherein the first air inlet channel is close to an edge of the bottom of the vaporization cavity relative to the second air inlet channel.

30. The air-curtain forming structure of claim 29, wherein the first air inlet channel is respectively provided on two opposite sides of the second air inlet channel.

31. The air-curtain forming structure of claim 28, wherein the air-curtain forming structure comprises a plurality of first air inlet channels, wherein the plurality of first air inlet channels are spaced apart from each other, and/or wherein a cross section of the first air inlet channel is strip-shaped.

32. The air-curtain forming structure of claim 1, wherein the air-curtain forming structure comprises a vaporizer applicable to the electronic vaporization device, wherein and the vaporizer comprises an air outlet channel, wherein the airflow channel is provided in the air outlet channel, and wherein the first air inlet channel is provided on a side wall of the air outlet channel such that the blocking airflow is formed between an inner wall of the air outlet channel and the vapor.

33. The air-curtain forming structure of claim 32, wherein the vaporizer further comprises a vaporization cavity in communication with the air outlet channel, and wherein the first air inlet channel is provided on a part of the air outlet channel close to the vaporization cavity.

34. The air-curtain forming structure of claim 32, wherein the vaporizer comprises a plurality of first air inlet channels sequentially spaced apart from each other in a circumferential direction of the air outlet channel.

35. The air-curtain forming structure of claim 32, wherein the first air inlet channel comprises a circular hole or an elongated hole.

36. An electronic vaporization device, comprising:

a main body; and an air-curtain forming structure, wherein the main body is connected to the air-curtain forming structure, and wherein the air-curtain forming structure comprises:

an airflow channel configured to deliver vapor, the airflow channel extending in an axial direction, the airflow channel having an inner wall, the inner wall extending parallel to the axial direction and circumferentially around the axial direction;

a first air inlet channel in communication with the airflow channel and configured to introduce an external airflow into the airflow channel so as to form a blocking airflow at a first radial distance relative to the vapor between the inner wall of the airflow channel and the vapor; and a second air inlet channel in communication with the airflow channel, the second air inlet channel being configured to introduce a second external airflow into the airflow channel so as to form a second airflow at a second radial distance relative to the vapor between the inner wall of the airflow channel and the vapor, wherein the first radial distance is greater than the second radial distance such that the blocking airflow is formed closer to the inner wall of the airflow channel than the second airflow.

* * * * *